United States Patent [19]
Loison et al.

[11] Patent Number: 5,821,079
[45] Date of Patent: Oct. 13, 1998

[54] VECTORS FOR THE EXPRESSION AND SECRETION OF HIRUDIN BY TRANSFORMED YEASTS

[75] Inventors: Gérard Loison, Strasbourg; Paul Tolstoshev, Mundolsheim; Yves Lemoine, Strasbourg; Jean-Pierre Lecocq, Reichstett, all of France

[73] Assignee: Transgene S.A., Courbevoie, France

[21] Appl. No.: 406,654

[22] Filed: Mar. 20, 1995

Related U.S. Application Data

[63] Continuation of Ser. No. 264,240, Jun. 22, 1994, abandoned, which is a continuation of Ser. No. 993,524, Dec. 16, 1992, abandoned, which is a continuation of Ser. No. 529,758, May 29, 1990, abandoned, which is a continuation of Ser. No. 14,042, filed as PCT/FR86/00153 May 2, 1986 published as WO86/06406 Nov. 6, 1986, abandoned.

[30] Foreign Application Priority Data

May 2, 1985 [FR] France .................................. 85 06672

[51] Int. Cl.$^6$ ............................ C12P 21/02; C12P 19/34; C12N 1/19; C12N 15/15
[52] U.S. Cl. ................... 435/69.1; 435/91.4; 435/254.2; 536/23
[58] Field of Search ........................ 536/23.5; 435/69.1, 435/71.2, 91.41, 91.42, 172.3, 320.1

[56] References Cited

U.S. PATENT DOCUMENTS

| | | | |
|---|---|---|---|
| 4,356,270 | 10/1982 | Itakura | 435/317 |
| 4,546,082 | 10/1985 | Kurjan et al. | 435/172.3 |
| 4,769,326 | 9/1988 | Rutter | 435/68 |

FOREIGN PATENT DOCUMENTS

| | | |
|---|---|---|
| 116201 | 8/1984 | European Pat. Off. . |
| 123294 | 10/1984 | European Pat. Off. . |
| 123544 | 10/1984 | European Pat. Off. . |
| 129073 | 12/1984 | European Pat. Off. . |
| 0168342 | 1/1986 | European Pat. Off. ......... C12N 15/00 |
| 8402921 | 8/1984 | WIPO . |
| 8603517 | 6/1986 | WIPO ............................ C12N 15/00 |

OTHER PUBLICATIONS

Woods et al J. Clin. Invest. vol. 74 pp. 634–638 (1984).
Molecular Biology of the Gene 3$^{rd}$ Ed. W.A. Benjamin, Inc p. 356 (1976.
Achsetter et al. EMBO J vol. 4, pp. 173–177 (1985).
Suggs et al (1981) PNAS 78: 6613–6617.
Bitter et al (1984) PNAS 81: 5330–5334.
Brake, et al (1984) PNAS 81: 4642–4646.
Chemical Abstracts, vol. 100, No. 19, 7 May, 1984; p. 227, ref. No. 152937g, Columbus, Hoio, US; J Dodt, et al The Complete Amino Acid Sequence of Hirudin, a Thrombin Specific Inhibitor. Application of Color Caboxymethylation—& Febs Lett. 1984 165(2), 180–4.

*Primary Examiner*—David Guzo
*Assistant Examiner*—William Sandals
*Attorney, Agent, or Firm*—Burns, Doane, Swecker & Mathis, L.L.P.

[57] ABSTRACT

Functional block of DNA enabling to prepare hirudine from yeast, characterized in that it comprises at least:—the gene of hirudine or one of its variants (gene H); —A DNA sequence ($S_{tr}$) comprising the signals providing for the transcription of the gene H by the yeast.

36 Claims, 17 Drawing Sheets

```
                                              1                    21
                                         a) GCA ATC TGC GTG TCT CAA GCA b) Ala Ile Cys Val Ser Gln Ala

Hinf I
      22                            ↓                              66
a)   ATT ACT TAC ACT GAT TGT ACA GAA TCG GGT CAA AAT TTG TGC CTC
      1                                                            15
b)   Ile Thr Tyr Thr Asp Cys Thr Glu Ser Gly Gln Asn Leu Cys Leu
      1   2
c)   Val Val  -----------------------------------------------------

67                                                            111
     TGC GAG GGA AGC AAT GTT TGC GGT AAA GGC AAT AAG TGC ATA TTG
     16                                                            30
     Cys Glu Gly Ser Asn Val Cys Gly Lys Gly Asn Lys Cys Ile Leu
                                           24
     ---------------------------------- Gln -----------------------

112                                                           156
     GGT TCT AAT GGA AAG GGC AAC CAA TGT GTC ACT GGC GAA GGT ACA
     31                                                            45
     Gly Ser Asn Gly Lys Gly Asn Gln Cys Val Thr Gly Glu Gly Thr
                 33      35  36
     ------ Asp ---- Glu ·Lys ---------------------------------

157                                                           201
     CCG AAC CCT GAA AGC CAT AAT AAC GGC GAT TTC GAA GAA ATT CCA
     46                                                            60
     Pro Asn Pro Glu Ser His Asn Asn Gly Asp Phe Glu Glu Ile Pro
         47          49                  53
     ---- Lys ·--- Gln --------- Asp ---------------------------
                                                            Aha III
                                                               ↓
     202                                                        256
     GAA GAA TAT TTA CAA TGAAAAATGAAAGAATATCAATCATAGAGAATTTTGATTT
     61               65
     Glu Glu Tyr Leu Gln

----------------------

257                                                           316
     AAAAACATTTCCATAGCTAAGCTATTTACCAATAAATAAATTAATTTTTCCATTGAATCT
     317                                                           372
     CAATCATATTTACTCTCAATCATATTCAGCTATTTACCAATAAATAAATTAATTTT
     373
     TCCATGA
```

FIG. 1

173
AGGGCCTTTGTTCCCATCAAAAATGTTACTGTTCTTACGATTCATTACGATTCAAGAATA
                                                         233
263
GTTCAAACAAGAAGATTACAAACTATCAATTCATACACAATATAAACGATTAAAAGA

293
ATG AGA TTT CCT TCA ATT TTT ACT GCA GTT TTA TTC GCA GCA TCC TCC
Met Arg Phe Pro Ser ILe Phe Thr Ala Val Leu Phe Ala Ala Ser Ser
                             323                              383

GCA TTA GCT GCT CCA GTC AAC ACT ACA GAA GAT GAA ACG GCA CAA
Ala Leu Ala Ala Pro Val Asn Thr Thr Glu Asp Glu Thr Ala Gln
         353                     413

ATT CCG GCT GTT GAA GCT GTC ATC GGT TAC TTA GAT TTA GAA GGG GAT TTC
ILe Pro Ala Val Glu Ala Val ILe Gly Tyr Leu Asp Leu Glu Gly Asp Phe
                                                 473

GAT GTT GCT GTT TTG CCA TTT TCC AAC AGC ACA AAT AAC GGG TTA TTG
Asp Val Ala Val Leu Pro Phe Ser Asn Ser Thr Asn Asn Gly Leu Leu
443

FIG. 2A

```
                                              803
                                               ↓
GGC CAA CCA ATG TAC  TAA  GCC CGA CTG ATA ACA ACA GTG TAG ATG TAA
Gly Gln Pro Met Tyr  ***

CAA AGT CGA C
```

FIG. 2C

FIG. 3
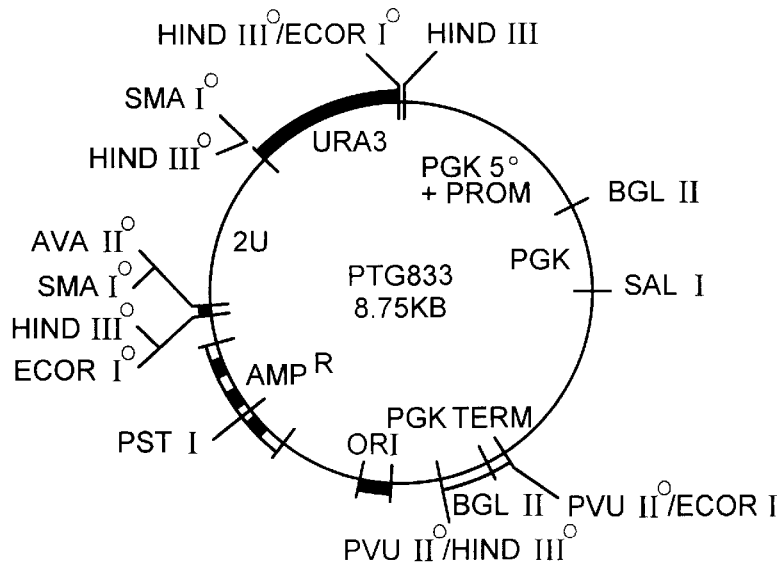
Partial digestion Bgl II
KLENOW TREATMENT
religation
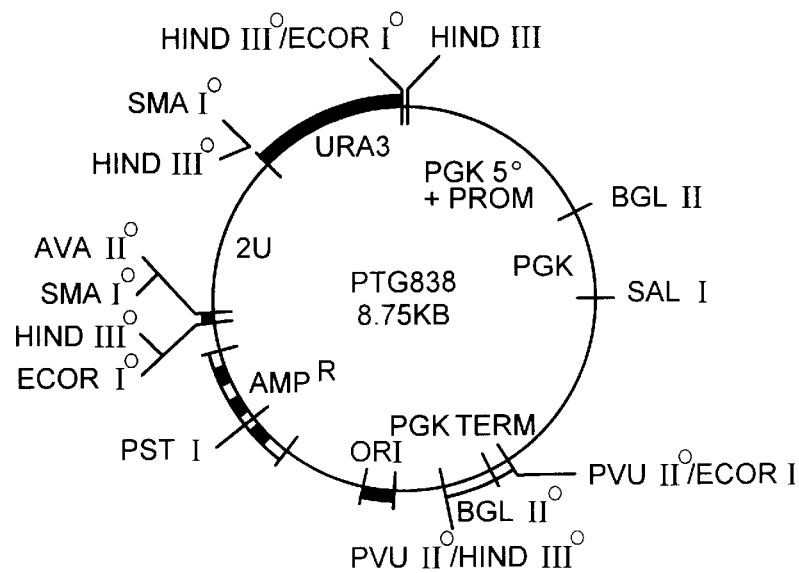

FIG. 7
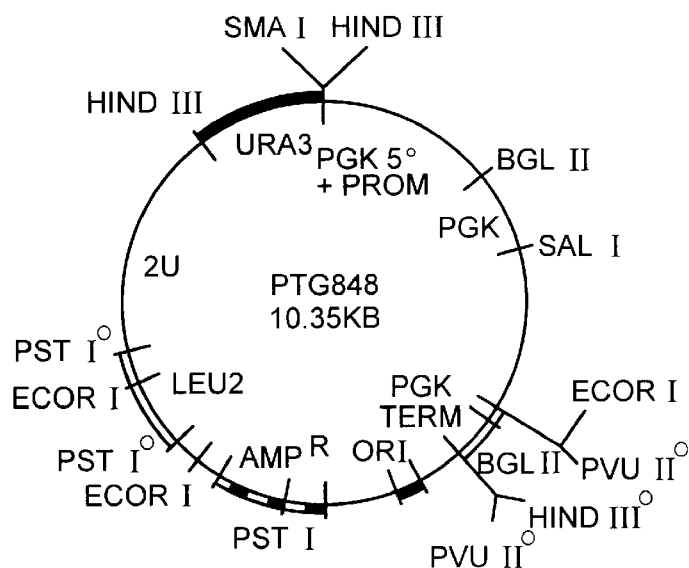
digestion with Hind III
Klenow treatment
Ligation in presence of Hind III
transformation in E.coli, pyr F⁻
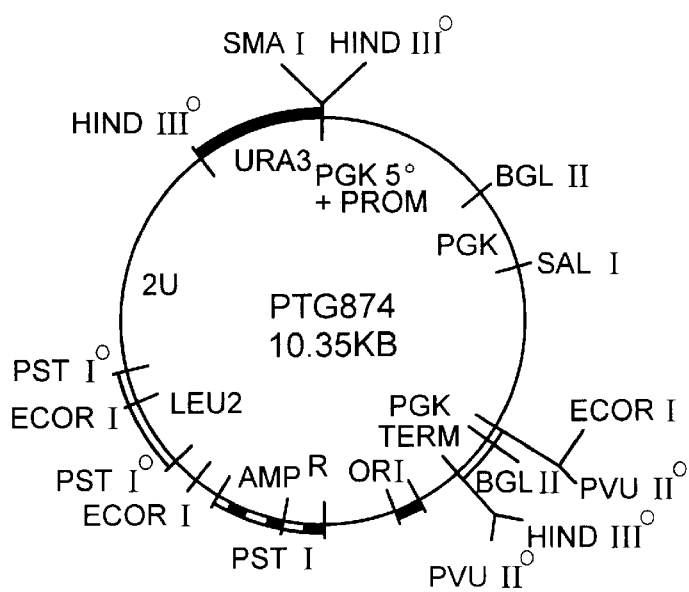

FIG. 9
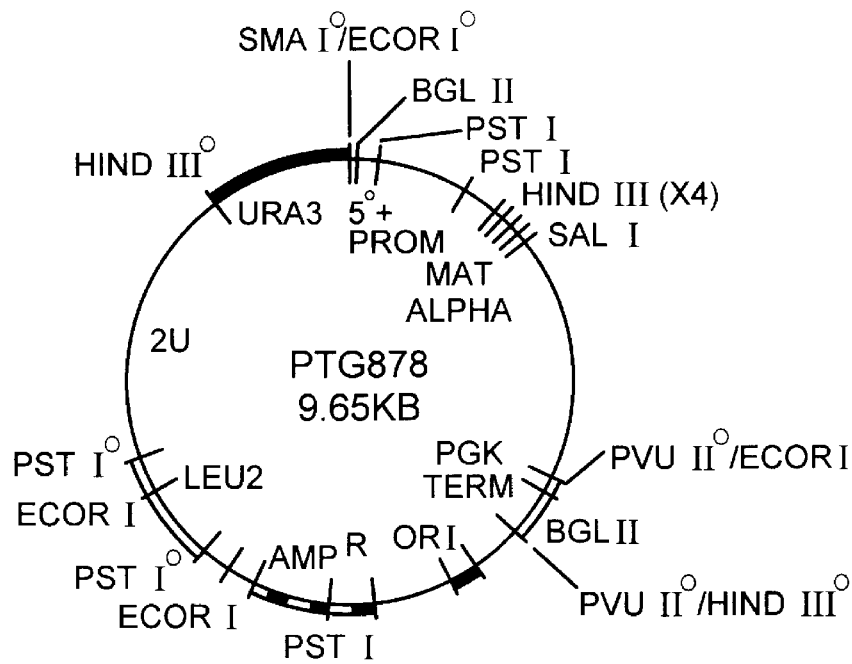
Partial Bgl II
Klenow treatment
religation
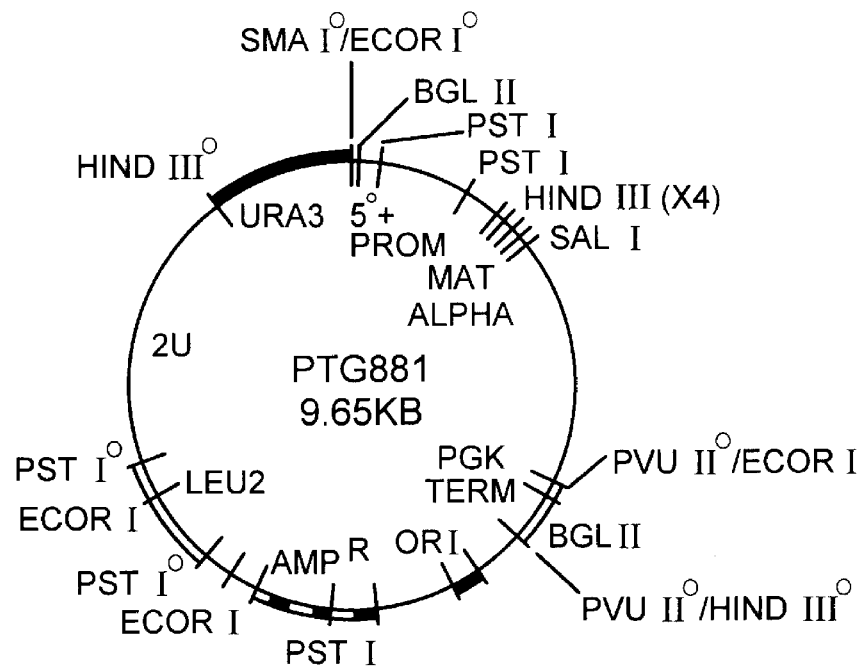

FIG. 11

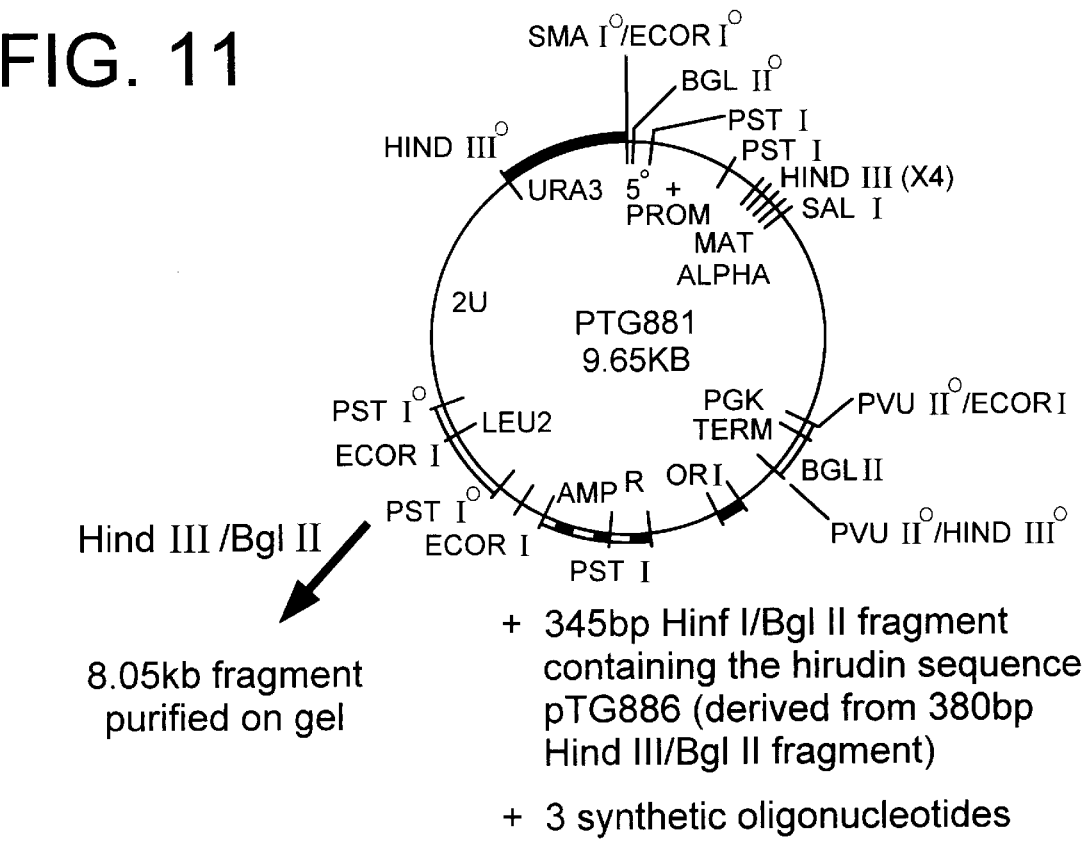

Hind III /Bgl II 8.05kb fragment
purified on gel

+ 345bp Hinf I/Bgl II fragment
containing the hirudin sequence
pTG886 (derived from 380bp
Hind III/Bgl II fragment)

+ 3 synthetic oligonucleotides

```
         11 mer            15 mer
        ┌─────────┐┌──────────────┐
        AGCTATTACGTATACAGACTGCACAG ┐Hinf I
Hind III┌TAATGCATATGTCTGACGTGTCTTA┘
        └─────────────────────────┘
                   25 mer
```

↓ PAIRING, LIGATION

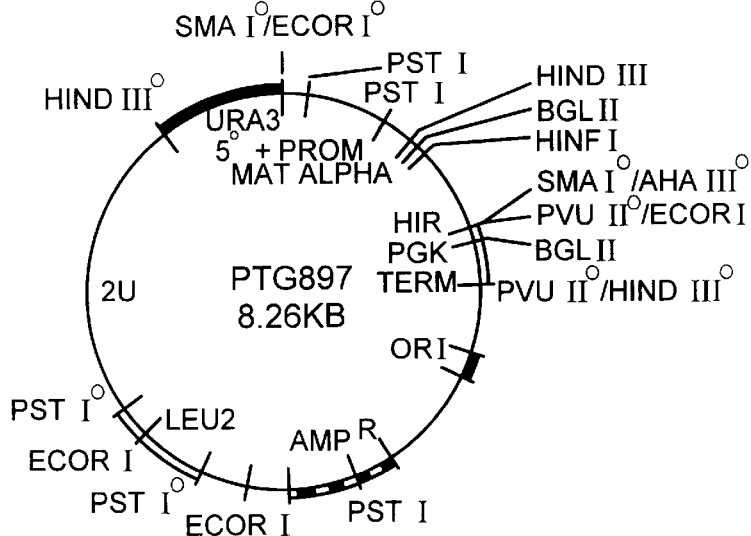

FIG. 14
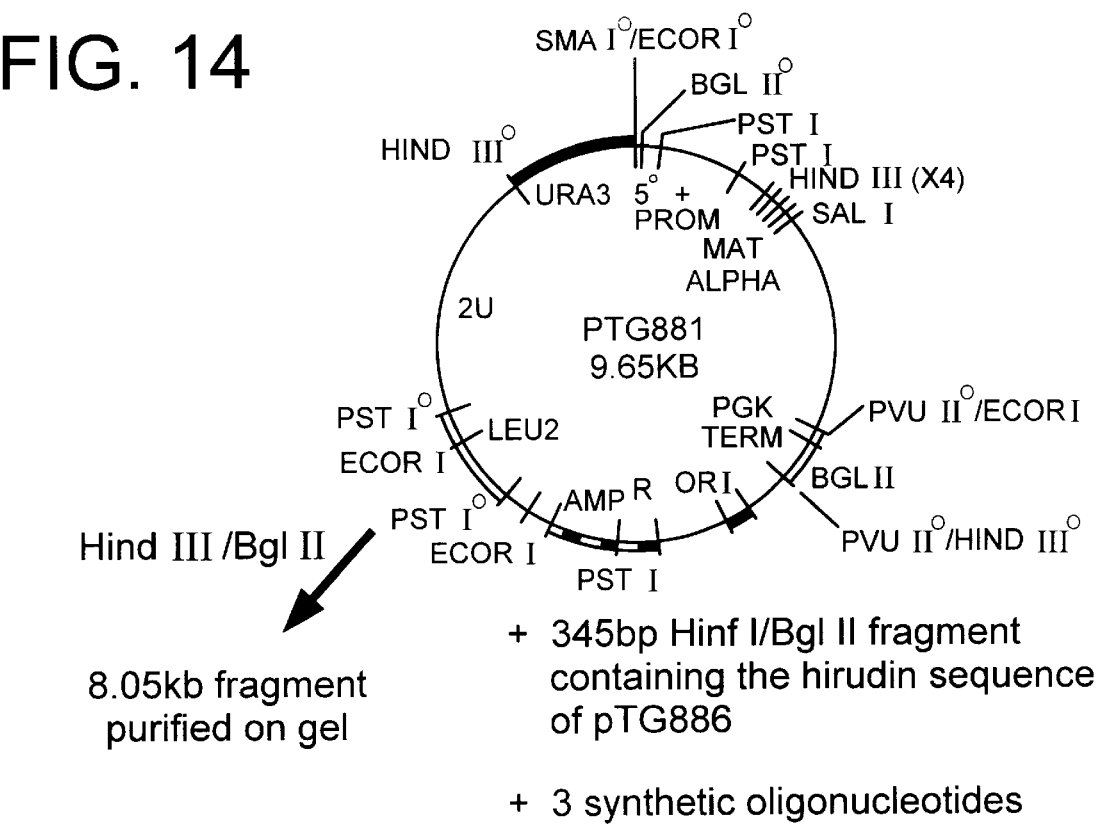
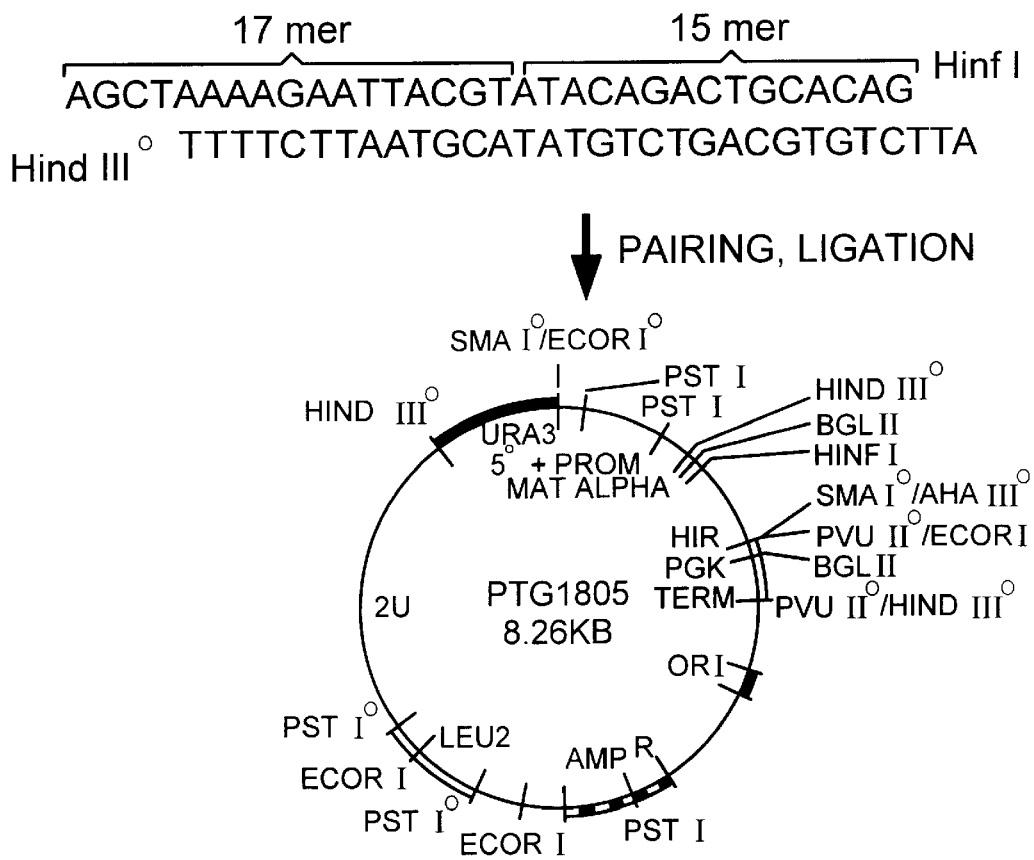

VECTORS FOR THE EXPRESSION AND SECRETION OF HIRUDIN BY TRANSFORMED YEASTS

This application is a continuation, of application Ser. No. 08/264,240, filed Jun. 22, 1994, which is a continuation of application Ser. No. 07/993,524 filed Dec. 16, 1992, which is a continuation of application Ser. No. 07/529,758 filed May 29, 1990, which is a continuation of application Ser. No. 07/014,042, filed as PCT/FR86/00153 May 2, 1986 published as WO86/06406 Nov. 6, 1986, all abandoned.

The present invention relates to vectors for the expression of the DNA sequence which codes for a hirudin or hirudin analogues, to the secretion of the hirudin into the culture medium of yeasts transformed by these vectors and to processes by means of which an active hirudin may be obtained by fermentation, and also to the hirudin obtained.

The anticoagulant activity present in the salivary glands of medicinal Leeches, *Hirudo medicinalis*, has its origin in a small polypeptide known as hirudin (1). This very specific and very effective inhibitor of thrombin has been widely studied in recent times, since it potentially offers a very useful therapeutic agent. Nevertheless, the extreme difficulty and cost of isolating and purifying it have prevented its being more widely used, and have even precluded the possibility of its being studied from the clinical standpoint.

The possibility of producing hirudin by cloning the genes and expressing them, using the recombinant DNA technique, has already been demonstrated by the cloning of a natural leech gene which codes for hirudin and expression in the microorganism *E. coli* (French Patent Application no. 84/04, 755 in the name of the Applicant Company, filed on 27th March 1984). Even though it has been possible to produce in *E. coli* a peptide having biological activity, it is very important to produce hirudin in other types of microorganisms. In effect, the clinical use of hirudin demands that the product be of very high purity, and the removal of pyrogenic contaminants might give rise to problems in the purification of hirudin from colibacillus extracts.

Moreover, the hirudin synthesized by *E. coli* remains intracellular, and must hence be purified from a very large number of *E. coli* peptides. For these reasons, it was useful to cause the hirudin gene to be expressed in yeast, which does not produce substances which are pyrogenic or toxic in man and which is capable of secreting proteins into the culture medium.

The mechanism of action of hirudin as an anticoagulant is only just beginning to be understood. The substrate for the binding of hirudin is thrombin, which is a proteolytic enzyme which, on activation (by activated factor X) from its zymogen form, prothrombin, cleaves fibrinogen in the circulation and converts it to fibrin which is necessary for the formation of the blood clot. The dissociation constant of the 1:1 thrombin-hirudin complex $(0.8 \times 10^{-10})$ indicates an extremely strong association between these molecules (2). In practice, the non-covalent complex between these two molecules can be considered to be indissociable in vivo.

Hirudin is a very specific inhibitor of thrombin, with a much higher affinity than the natural substrate, fibrinogen. Moreover, it is not necessary for other coagulation factors or other plasma constituents to be present. The specific and very substantial antithrombin activity of hirudin makes it obvious that it can be applied clinically as an anticoagulant.

Hirudin has been studied to a very considerable extent in animals on account of its anticoagulant properties. The most detailed study (3) describes the activity of hirudin in the prevention of venous thromboses, vascular occlusions and disseminated intravascular coagulations (DIC) in rats. Hirudin is well tolerated by rats, dogs, rabbits and mice when it is in a very purified form and is injected intravenously. The $LD_{50}$ in mice is greater than 500,000 U/kg of body weight (that is to say 60 mg/kg). Another study (4) shows that mice tolerate doses ranging up to 1 g/kg and that rabbits tolerate up to 10 mg/kg both intravenously and subcutaneously. In mice, repeated injections for a period of two weeks do not lead to sensitization reactions.

Moreover, in experimental animals, hirudin is rapidly eliminated (half-life of the order of 1 hour), still in a biologically active form, via the kidneys (3).

Two other independent studies, one using dogs (5) and the other (6) showing the activity of hirudin in the prevention of DIC in rats, are in agreement with the positive results of Markwardt and his co-workers. These investigators have recently published the first in vivo analysis of the effects of natural hirudin on the human haemostatic system (7). The subject showed the expected biological effects without any sign of toxic side effects.

It was also possible to demonstrate that hirudin prevents endotoxin-induced DIC in pigs (8), and thus constitutes a potential solution to the very serious problems caused by endotoxaemias which lead to a high mortality in pigs.

A single very recent publication (7) describes the intravenous and subcutaneous administration of hirudin to humans. Six volunteers were used to evaluate the pharmacokinetics and the effects on the haemostatic system of a single dose (1,000 AT-U/kg) of hirudin. When administered intravenously, hirudin has a half-life of 50 minutes, and 50% of the hirudin appears in an active form in the urine during 24 hours after the injection. A prolongation is observed in the coagulation time (measured in vitro for thrombin, thromboplastin and prothrombin) according to the concentration of hirudin in the plasma, showing that the molecule retains its biological activity in the subject's circulation. No change is observed in the number of platelets, in the fibrinogen level or in the fibrinolytic system. Like the intravenous injections, subcutaneous injections of hirudin are well tolerated and do not cause any side effects. To test for the possible appearance of allergic reactions, 2 intracutaneous injections were administered to the same subjects at an interval of 4 weeks; no sign of sensitization was observed. Moreover, no anti-hirudin antibodies are detected in the serum.

These studies suggest that hirudin can constitute a clinical agent which is useful as an anticoagulant. As a result of the high specificity of action of hirudin, the pre-phase of blood coagulation is not affected. The antithrombin activity is dose-dependent, and the effect of hirudin is rapidly reversible as a result of its rapid renal elimination. It has been possible to demonstrate that hirudin is far superior to heparin for the treatment of DIC (3, 6), as could be expected in view of the fact that DIC is accompanied by a decrease in antithrombin III (a cofactor required for the action of heparin) and a release of platelet factor 4 which is a very effective antiheparin agent.

One study has demonstrated the possibility that hirudin may be absorbed by the skin of humans (9), although the results obtained remain somewhat difficult to interpret.

Commercial preparations of acellular crude extracts of leeches are available as an ointment (Hirucrème, Societé Nicholas, France; Exhirud-Blutgel, Plantorgan Werke, West Germany), but further tests with larger doses of a highly purified material are required in order to establish whether this is an advantageous administration route. In general, the preferred administration routes are the intravenous and intramuscular routes and the percutaneous route. Other administration routes have been reported for hirudin, in particular the oral route (BSM no. 3,792 M).

In combination with other components, this product can also be used in the treatment of psoriasis and other skin disorders of the same type, as is described in German Offenlegungsschrift 2,101,393.

Hirudin can, moreover, be used by way of anticoagulant in clinical laboratory tests and as a research tool. In this case, the high specificity for a single stage in the coagulation of blood can have a considerable advantage relative to the most frequently used anticoagulants, the action of which is much less specific.

Moreover, hirudin can be very useful as an anticoagulant agent in extracorporeal circuits and in dialysis systems, where it can have considerable advantages relative to other anticoagulants, especially if it can be immobilized in an active form on the surface of these artificial circulatory systems.

The binding activity of hirudin to thrombin can, moreover, make possible the indirect protection of coagulation factors such as factor VIII, during its purification.

Finally, the use of labelled hirudin can constitute a simple and effective method for measuring thrombin and prothrombin levels. In particular, labelled hirudin can be used in order to visualize clots in the process of formation, since the phenomenon of coagulation involves the conversion of circulating prothrombin to thrombin at the site of formation, the labelled hirudin becoming bound to the thrombin and having the capacity to be visualized.

It is, moreover, possible to envisage the direct use of transformed yeasts by way of a drug which releases hirudin, for example by spreading a cream containing the said yeasts which secrete hirudin onto the skin.

In summary, the hirudin according to the invention has a large number of possible applications:

1) as an anticoagulant in critical thrombotic conditions, for prophylaxis and for preventing the extension of existing thromboses;
2) as an anticoagulant for reducing haematomas and swellings after microsurgery, in which situations considerable use is made of live leeches;
3) as an anticoagulant in extracorporeal circulation systems and as an anticoagulant agent for coating synthetic biomaterials;
4) as an anticoagulant in clinical tests on blood samples in laboratory experiments;
5) as an anticoagulant in clinical research on coagulation, and as an experimental tool;
6) as a possible topical agent for cutaneous application in the treatment of haemorrhoids, varicose veins and oedema;
7) as a component in the treatment of psoriasis and other related disorders;
8) Lastly, the hirudin can be used for binding thrombin during the storage of blood and the preparation of blood derivatives (platelets, factors VIII and IX).

As a guide, hirudin can be used in therapeutic compositions at concentrations corresponding to 100–50,000 antithrombin U/kg per day.

Since hirudin is soluble in water, it is simple to obtain injectable pharmaceutical compositions or pharmaceutical compositions applicable by other routes using pharmaceutically acceptable carriers and vehicles.

Lastly, it is possible to use hirudin labelled either with a radioactive label or with any other type of enzyme or fluorescent label, the labelling being carried out by known techniques, in order to perform in vitro assays or in vivo imaging, especially for visualizing clot formation.

A preparation of hirudin from the whole animal has been used for determining the amino acid sequence of the protein (10, 11). In the experiments which follow, a gene has been cloned which is expressed as a messenger RNA in the heads of fasted leeches. This gene carries information for a protein (hirudin variant 2 or HV-2), the sequence of which is significantly different from that found in the whole body of the animal (protein variant known as HV-1). There are 9 differences in amino acid residues between HV-1 and HV-2, and the differences between the two $NH_2$-terminal residues (Val-val or Ile-thr) may explain the apparent contradictions in the literature regarding the $NH_2$-terminal end of hirudin (12).

FIG. 1 shows the DNA sequences of the recombinant plasmid pTG717 which contains a copy of the cDNA corresponding to the HV-2 mRNA, as well as, at b), the amino acid sequence deduced from the DNA sequence and, at c), the differences between this sequence and the amino acid sequence of HV-1.

It is appropriate to note that the cDNA sequence is probably incomplete and that there may be a signal sequence upstream of the beginning of the mature protein.

Expression of the HV-2 cDNA in microorganisms shows that the corresponding protein has antithrombin activity.

Although the experiments below were carried out with the HV-2 variant, in that which follows, except where otherwise stated, "hirudin" and "gene which codes for hirudin" will be used to denote either variant, that is to say HV-1 or HV-2, and similarly other possible variants, and the corresponding sequences.

One of the subjects of the present invention is the preparation of hirudin by yeasts.

Yeasts are unicellular eukaryotic organisms. The Saccharomyces genus of yeast comprises strains, the biochemistry and genetics of which are studied intensively in the laboratory; it also comprises strains used in the foodstuffs industry (bread, alcoholic drinks, and the like), which are consequently produced in very Large quantities.

The facility with which the genetics of *saccharomyces cerevisiae* cells can be manipulated, either by classical techniques or by techniques derived from genetic engineering, and still better by a combination of these two types of technique, and the long industrial history of this species make it a host of choice for the production of foreign polypeptides.

For this reason, the present invention relates more especially to a functional DNA block which enables hirudin to be prepared from yeast, characterized in that it contains at least:

the gene for hirudin or one of its variants (hereinafter H gene);

a DNA sequence ($S_{rr}$) containing the signals which provide for transcription of the H gene by yeast.

When integrated in a plasmid or in the chromosomes of a yeast, preferably of the genus Saccharomyces, this functional block may, after transformation of the said yeast, enable hirudin to be expressed, either in an active form or in the form of an inactive precursor capable of regenerating hirudin on activation.

The value of *Saccharomyces cerevisiae* is that this yeast is capable of secreting some proteins into the culture medium, great advances are being made in the study of the mechanisms responsible for this secretion, and it has been shown that it was possible, after appropriate manipulations, to make the yeast secrete correctly processed human hormones which were in all respects similar to those found in human serum (13, 14).

In the context of the present invention, this property is turned to good account to obtain the secretion of hirudin, since this offers many advantages.

In the first place, yeast secretes few proteins, which has the advantage, if direction of secretion of a given foreign protein can be achieved at a high level, of enabling a product to be obtained in the culture medium which can represent a high percentage of total secreted proteins, and hence of facilitating the work purifying the protein sought.

Several proteins or polypeptides are secreted by yeast. In all known cases, these proteins are synthesized in the form of a longer precursor, the $NH_2$-terminal sequence of which is crucial for entry into the metabolic pathway leading to secretion.

The synthesis in yeast of hybrid proteins containing the $NH_2$-terminal sequence of one of these precursors followed by the sequence of the foreign protein can, in some cases, lead to the secretion of this foreign protein. The fact that this foreign protein is synthesized in the form of a precursor, which is hence generally inactive, enables the cell to be protected against the possible toxic effects of the molecules sought, the cleavage which liberates the active protein only taking place in vesicles, derived from the Golgi apparatus, which isolate the protein from the cytoplasm.

Use of the metabolic pathways leading to secretion to make the yeast produce a foreign protein hence has several advantages:

1) it enables a reasonably pure product to be recovered in the culture supernatant;
2) it enables the cell to be protected against the possible toxic effects of the mature protein;
3) furthermore, the proteins secreted can, in some cases, undergo modifications (glycosylation, sulfation, and the like).

For this reason, the expression blocks according to the invention will have, more especially, the following structure:

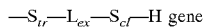

$L_{ex}$ codes for a Leader sequence required for the excretion of the protein corresponding to the H gene; $S_{cl}$ is a DNA sequence coding for a cleavage site ; moreover, the element $S_{cl}$—H gene can be repeated several times.

As an example of a secretion system, that of the alpha pheromone was chosen, that is to say, in the above sequence, the sequence $L_{ex}$ originates from the gene for the alpha sex pheromone of yeast, but other systems could be used (for example, the Killer protein system) (13).

The alpha sex pheromone of yeast is a peptide consisting of 13 amino acids (shown boxed in FIG. 2) which is secreted into the culture medium by S. cerevisiae yeasts of sex type MATα. The alpha factor arrests the cells of the opposite sex type (MATa) in phase G1, and induces biochemical and morphological changes required for the mating of the two types of cells. Kurjan and Herskowitz (16) have cloned the structural gene for the α factor and have deduced from the sequence of this gene that this 13-amino acid α factor was synthesized in the form of a 165-amino acid precursor preproprotein (FIG. 2). The precursor contains an amino-terminal hydrophobic sequence of 22 residues (broken underlining) followed by a sequence of 61 amino acids containing 3 glycosylation sites, finally followed by 4 copies of the α factor. The 4 copies are separated by "spacer" sequences and the mature protein is liberated from the precursor as a result of the following enzyme activities:

1) an endopeptidase of the cathepsin B type which cuts at the COOH side of Lys-Arg dipeptides (cleave site indicated by a broad arrow);
2) an exopeptidase of the carboxypeptidase B type which cuts off the basic residues present at the COOH end of the excised peptides;
3) a dipeptidyl aminopeptidase (known as A) which removes the Glu-Ala and Asp-Ala residues.

The nucleotide sequence of this precursor contains in addition, 4 HindIII restriction sites, indicated by an arrow H.

Several fusions were carried out between the α pheromone gene and the mature hirudin sequence. Yeast cells of the MATα type can express these fused genes. The corresponding hybrid proteins can then be processed as a result of the signals which they contain, which originate from the prepro-sequences of the α pheromone precursor. It is consequently expected that polypeptides having the hirudin sequence will be recovered in the culture supernatant.

In one of these constructions, the $S_{cl}$ sequence contains an ATG codon at the 3' end preceding the H gene; the fused protein hence contains a methionine immediately upstream of the first amino acid of the mature hirudin sequence. After cleavage with cyanogen bromide, this polypeptide yields a hirudin molecule which can be made active after a renaturation stage.

In other constructions, the cleavage signals normally used for producing the pheromone serve to produce, in the culture supernatant, polypeptides possessing antithrombin activity. This is the case when the sequence $S_{cl}$ contains two codons which code for Lys-Arg, that is to say AAA or AAG with AGA or AGG, at its 3' end; the polypeptide is cut by an endopeptidase which cuts off Lys-Arg dipeptides on the COOH side, thereby liberating hirudin.

In particular, the invention relates to the constructions in which the sequence preceding the hirudin gene codes for one of the following amino acid sequences;

1) Lys Arg Glu ALa Glu Ala Trp Leu Gln VaL Asp Gly Ser Met hirudin . . . ,
2) Lys Arg Glu Ala Glu Ala hirudin . . . ,
3) Lys Arg Glu Ala Glu Ala Lys Arg hirudin . . . ,
4) Lys Arg Glu Ala Glu Ser Leu Asp Tyr Lys Arg hirudin or
5) Lys Arg hirudin . . .

It is, of course, possible to envisage using other sequences which, at the amino acid level, are selectively cut with an enzyme, with the proviso that this cleavage site must not also be present in hirudin itself.

Finally, the expression blocks may possess, after the H gene, a yeast terminator sequence, for example that of the PGK gene.

In general, the expression blocks according to the invention may be integrated in a yeast, especially Saccharomyces, either in an autonomously replicating plasmid or in the yeast chromosome.

When the plasmid is autonomous, it will contain elements providing for its replication, that is to say an origin of replication such as that of the 2 μ plasmid. In addition, the plasmid may contain selection elements, such as the URA3 or LEU2 gene, which provide for complementation of ura3⁻ or Leu2⁻ yeasts. These plasmids can also contain elements which provide for their replication in bacteria, when the plasmid has to be a "shuttle" plasmid, for example an origin of replication such as that of pBR322, a marker gene such as $Amp^r$ and/or other elements known to those versed in the art.

The present invention also relates to yeast strains transformed by an expression block according to the invention, either carried by a plasmid or integrated in its chromosomes. Among these yeasts, yeasts of the genus Saccharomyces, in particular S. cerevisiae, must be mentioned more especially.

When the promotor is that of the α pheromone gene, the yeast will preferably be of the MATα sex type. For example, a strain of genotype ura3⁻ or leu2⁻, or the like, complemented by the plasmid to provide for maintenance of the plasmid in the yeast by application of an appropriate selection pressure, will be used.

Although it is possible to prepare hirudin by fermentation of the above transformed strains in a suitable culture medium, by accumulation of hirudin in the cells, it is nevertheless preferable, as emerges from the above description, to cause the hirudin to be secreted into the medium, either in mature form or in the form of a precursor which will have to be processed in vitro.

This maturation can be carried out in several stages. First, it may be necessary to cleave certain elements originating from the translation of the sequence $L_{ex}$, and this cleavage will be performed on the sequence corresponding to $S_{cl}$. As stated above, mature hirudin can be preceded by a methionine which will be selectively cleaved by cyanogen bromide. This method can be used because the sequence coding for hirudin does not include methionine.

It is also possible to provide, at the N-terminal end, the Lys-Arg dipeptide which is cut on the COOH side by a specific endopeptidase; since this enzyme is active in the secretion process, it is hence possible, in this manner, to obtain the mature protein directly in the medium. However, in some cases, it may be necessary to provide for enzymatic cleavage after secretion, by adding a specific enzyme.

In some cases, especially after treatment with cyanogen bromide, it may be necessary to renature the protein by re-forming the disulphide bridges. To this end, the peptide is denatured, for example with guanidinium hydrochloride, and then renatured in the presence of reduced and oxidized glutathione.

Finally, the invention relates to the hirudin obtained by the processes according to the invention.

Other characteristics and advantages of the present invention will emerge on reading the examples below.

In the attached figures:

FIG. 1 shows the nucleotide sequence of the cDNA fragment of hirudin cloned in pTG 717;

FIG. 3 shows schematically the construction of pTG834;

FIG. 7 shows schematically the construction of pTG874;

FIG. 9 shows schematically the construction of pTG881;

FIG. 11 shows schematically the construction of pTG897;

FIG. 14 shows Schematically the construction of pTG1805;

FIG. 16 is a diagram comparing the amino acid sequences downstream from the first cleavage site (Lys-Arg) in different constructions.

The amino acid and nucleotide sequences are not repeated in the present description so as not to encumber the latter, but they form an explicit part thereof.

EXAMPLE 1

Construction of pTG822

A cDNA fragment of hirudin HV-2 was extracted from a gel after digestion of plasmid pTG717 with PstI, and then digested at the same time with the enzymes HinfI and AhaIII. The enzyme HinfI cuts downstream of the first codon of the mature hirudin HV-2 sequence. The enzyme AhaIII cuts approximately 30 base pairs behind (3') the stop codon of the hirudin sequence. The HinfI-AhaIII fragment thereby obtained was isolated on agarose gel and then eluted from this gel.

The sequence which codes for the mature protein was introduced into vector pTG880. Vector pTG880 is a derivative of vector pTG838 (FIG. 3). Plasmid pTG838 is identical to pTG833 except as regards the BglII site situated near the PGK transcription terminator. This site has been eliminated by the filling-in action of Klenow polymerase to give pTG838.

Plasmid pTG833 is a yeast/*E.coli* shuttle plasmid. This plasmid was designed for expressing foreign genes in yeast. The basic elements of this vector (FIG. 3) are as follows: the URA3 gene as a selection marker in yeast, the origin of replication of the yeast 2μ plasmid, the gene for resistance to ampicillin and the origin of replication of *E. coli* plasmid pBR322 (these latter two elements enabling this plasmid to be propogated and selected in colibacille), the 5' flanking region of the yeast PGK gene with the sequence which codes for this gene up to the SalI site, the SalI-PvuII fragment of pBR322 and the PGK gene terminator (19). This plasmid has already been described in French Patent Application no. 84/07,125 in the name of the Applicant Company, filed on 9th May 1984.

Figure 4:
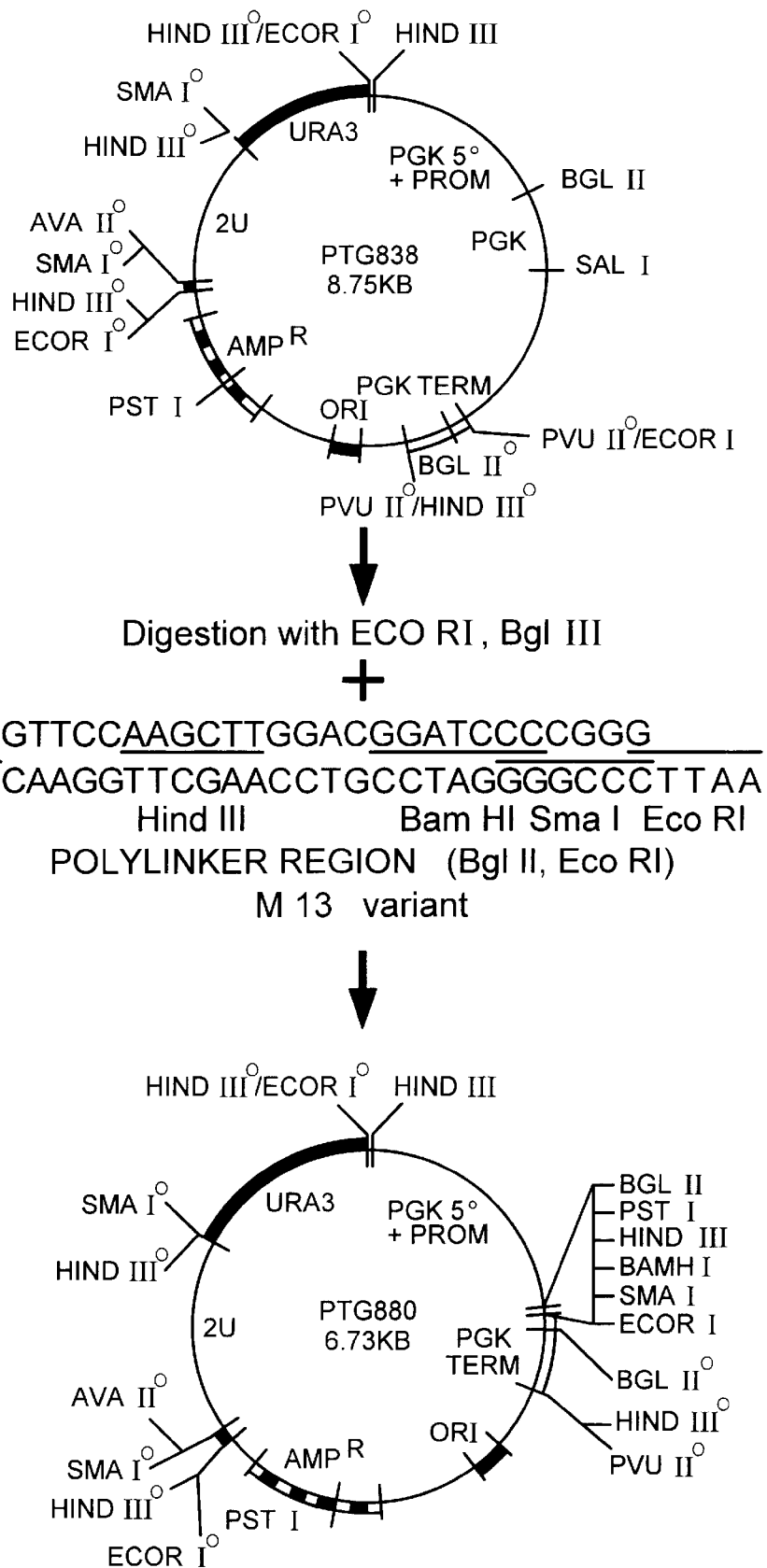
FIG. 4 shows schematically the construction of pTG880.
Figure 5:
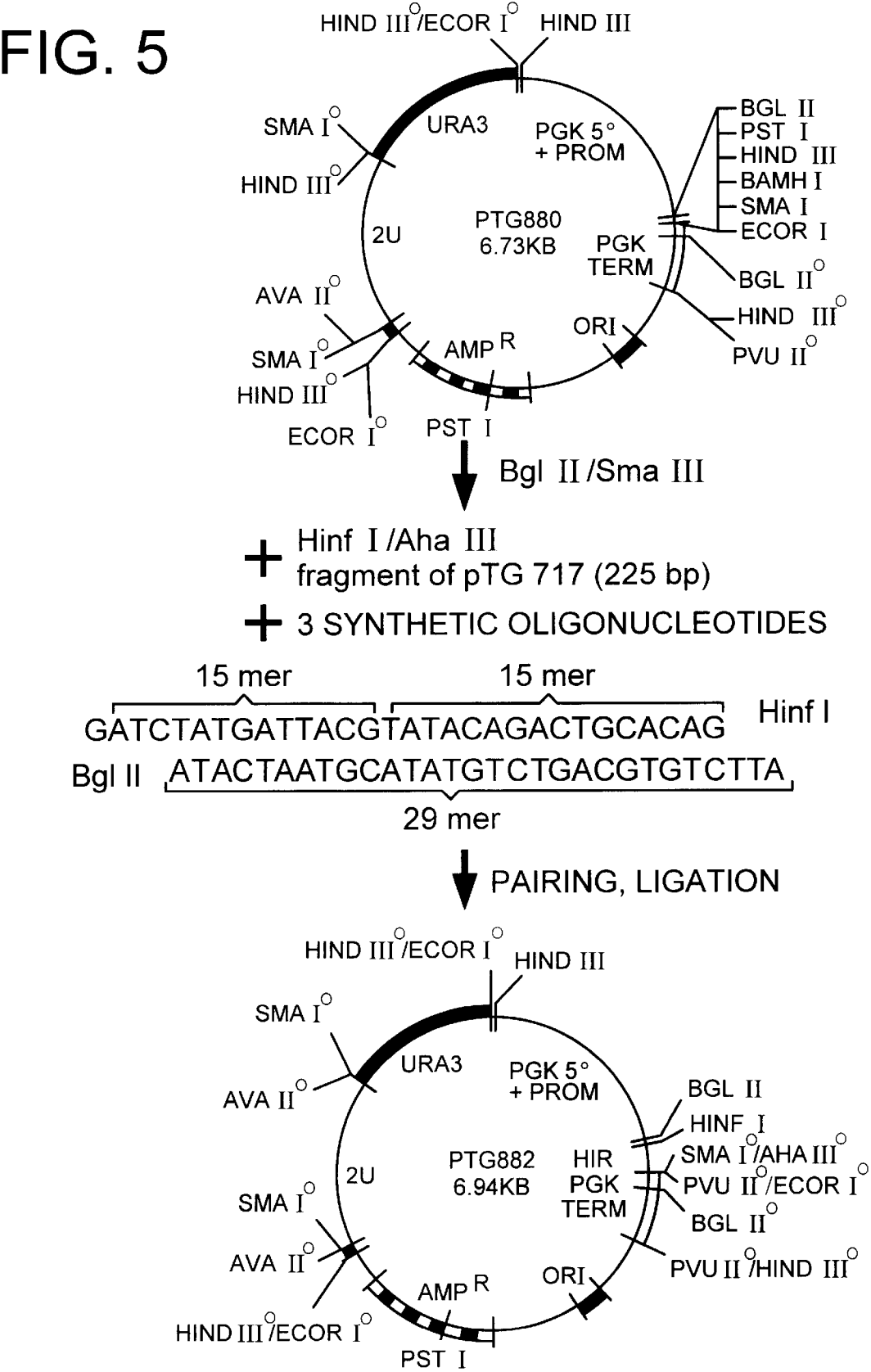
FIG. 5 shows schematically the construction of pTG882.

Plasmid pTG880 was constructed from pTG838 (FIG. 4) by insertion of a short polylinker region (derived from a bacteriophage M13) into pTG838 cut with EcoRI and BglII, which enables a series of cloning sites to be positioned, in the order BglII, PstI, HindIII, BamHI, SmaI and EcoRI, immediately after the 5' region flanking the yeast PGK gene. The DNA of plasmid pTG880 was digested with BglII and SmaI, and the large fragment emerging from this digestion was isolated and eluted from a gel. The HinfI-AhaIII fragment of pTG717, which contains most of the sequence coding for hirudin HV-2, was mixed with digested pTG880 at the same time as 3 synthetic oligonucleotides (FIG. 5) intended to reconstitute the NH₂ terminal region of the hirudin sequence, the nucleotides re-Linking the BglII site of the vector to the HinfI site of the fragment containing the hirudin. This mixture was subjected to a ligation treatment and then served to transform *E. coli* cells. Plasmid pTG882 was recovered in transformants.

This plasmid served to transform yeast cells with the object of producing hirudin under the control of the PGK promoter. However, no hirudin activity was detected in the crude extracts of cells transformed with this vector. The reason for the Lack of active hirudin production is still not clear. However, the construction pTG882 served as a source of the hirudin-coding sequence for the yeast secretion vectors described below.

EXAMPLE 2

Construction of pTG886 and pTG897

Figure 6:
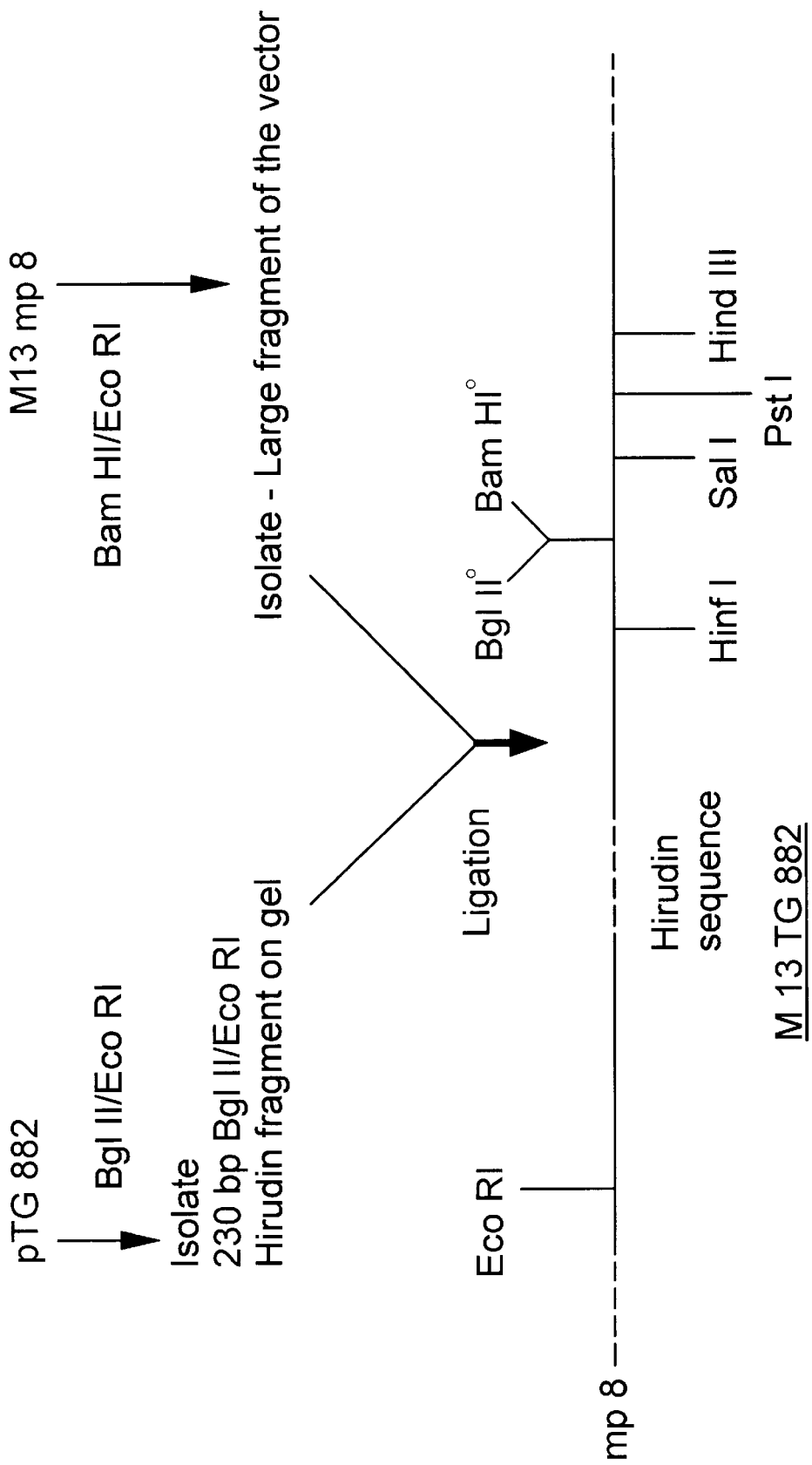
FIG. 6 shows schematically the construction of M13TG882.

First, the BglII-EcoRI fragment (230 bp) of pTG882 containing the hirudin sequence was transferred to bacteriophage M13mp8 (FIG. 6) between the BamHI and EcoRI sites. This gave the phage M13TG882, from which it was possible to isolate an EcoRI-HindIII fragment (approximately 245 bp). This fragment contains the entire coding sequence for hirudin HV-2, the BamHI/BglII fusion site and cohesive ends (HindIII-EcoRI) which enable it to be cloned in the yeast secretion vector pTG881 (FIG. 9).

Plasmid pTG881 (10 kb) is an *E. coli*/yeast shuttle plasmid which replicates autonomously both in *E. coli* and in *Saccharomyces cerevisiae* strains, uvarum and carlbergensis.

The introduction of this plasmid into *E. coli* enables resistance to ampicillin (and other β-Lactam type antibiotics) to be obtained. In addition, this plasmid carries the yeast genes LEU2 and URA3, which are expressed in strains of *E. coli* and Saccharomyces. The presence of this plasmid *E. coli* or in Saccharomyces hence enables complementation to be obtained of strains deficient in β-isopropylmalate dehydrogenase or OMP decarboxylase.

Plasmid pTG881 is constructed in the following manner:

The starting plasmid is pTG848 (identical with pTG849 described in French Patent no. 83/15,716 with the exception of the ura3 gene, the direction of which is reversed), and it consists of the following DNA fragments (FIG. 7):

1) The approximately 3.3 kb EcoRI-HindIII fragment derived from plasmid pJD8207 (17). The HindIII site corresponds to the coordinate 105 of the 2μ plasmid, B form, the EcoRI site to the coordinate 2243. In this fragment, the LEU2 gene has been inserted by polydeoxyadenylate/polydeoxythymidylate extension in the PstI site of the B form 2μ fragment (17);
2) The HindIII fragment of the URA3 gene (18);
3) The large EcoRI (coordinate 0)-SalI (coordinate 650) fragment of pBR322. In the PvuII site of this fragment, there has been inserted the 510 base pair EcoRI-HindIII fragment (the ends of which have previously been made blunt by the action of Klenow enzyme in the presence of the 4 nucleotides) corresponding to the end of the PGK gene (19). When joined to the PvuII end of pBR322, the squared-off EcoRI end of the PGK gene regenerates an EcoRI site;
4) The HindIII-SalI fragment (2.15 kb) of the PGK gene (19).

Plasmid pTG848 cut with HindIII, and the ends of the two fragments thereby liberated are made blunt by treatment with Klenow enzyme in the presence of the 4 deoxyribonucleotides. Ligation of the two fragments is carried out and, before transformation, this Ligation mixture is subjected to the action of HindIII, which enables any plasmid form which has retained a HindIII site (or two such sites) to be removed. *E. coli* strain BJ5183 (pyrF) is transformed and the transformants are selected for resistance to ampicillin and for the pyr+ character. Plasmid pTG874 is thereby obtained (FIG. 7), in which the two HindIII sites are eliminated, the orientation of the URA3 gene giving rise to transcription in the same direction as that of the phosphoglycerate kinase (PGK) gene.

Figure 8:
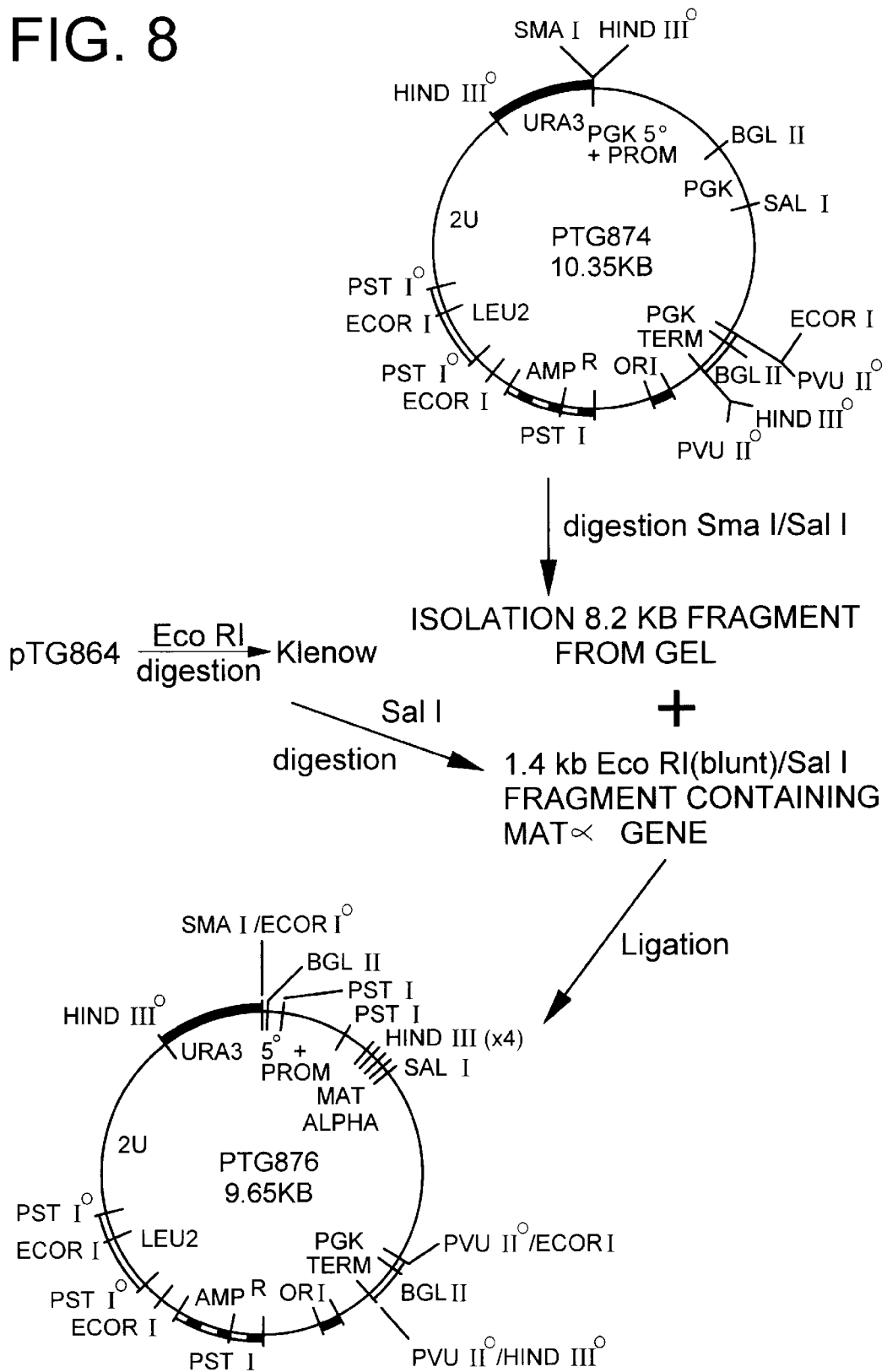
FIG. 8 shows schematically the construction of pTG876.

Plasmid pTG874 is cut with SmaI and SalI, and the 8.6 kb fragment is then isolated from an agarose gel. The plasmid pTG864, which comprises the EcoRI-SalI fragment (approximately 1.4 kb) of the MFα1 gene cloned in the same sites of pBR322, is cut with EcoRI. The ends of the plasmid which has been linearized in this way are made blunt by the action of Klenow enzyme in the presence of the 4 nucleotides. Digestion is then performed with the enzyme SalI, and the EcoRI (blunt end)-SalI fragment corresponding to the MFα1 gene is isolated. This latter fragment is ligated with the SmaI-SalI piece (8.6 kb) of pTG874, thereby giving plasmid pTG876 (FIG. 8).

In order to eliminate the proximal BglII site of the MFα1 promotor sequence, partial digestion of plasmid pTG876 with BglII was followed by the action of Klenow enzyme in the presence of the 4 deoxyribonucleotides. The new plasmid obtained, pTG881 (FIG. 9), permits the insertion of foreign coding sequences between the first HindIII site of the MFα1 gene and the BglII site of the end of the PGK gene.

When fusion at the HindIII site of the foreign coding DNA enables translation to be obtained in the same reading phase, the hybrid protein obtained comprises the prepro-portions of the α pheromone.

Figure 10:
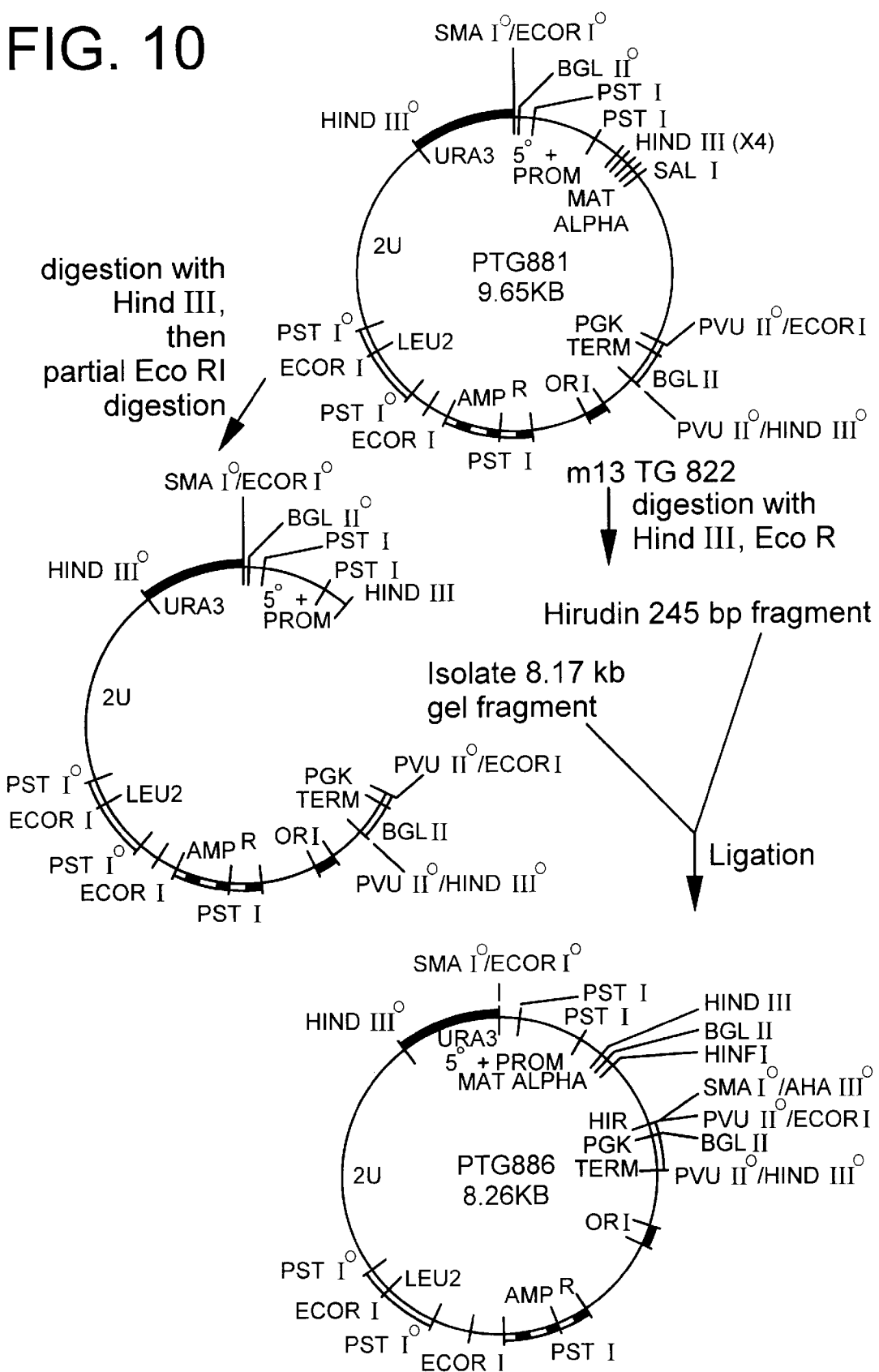
FIG. 10 shows schematically the construction of pTG886.

Cloning in pTG881 of the HindIII-EcoRI fragment which carries the hirudin gene leads to plasmid pTG886 (FIG. 10). When the cloning has been carried out, there is a BglII site downstream from the fragment, and this enables the fragment to be extracted again in a HinfI-BglII form, the HinfI site being the same as that used above. Since there is only a single BglII site in pTG881, it is very easy to reconstitute the 5' end of the sequence which codes for hirudin, using 3 oligonucleotides which reconstitute the 5' sequence of hirudin and enabling the prepro-sequence of the αpheromone followed by the mature hirudin sequence to be read in phase.

This new plasmid is known as pTG897 (FIG. 11).

EXAMPLE 3

Expression of hirudin by yeasts

The DNA of pTG897 was used to transform a TGY1sp4 (MATα, ura3 -251 -373 -328, his3 -11-15) yeast to ura+ according to a technique already described (20).

A transformed colony was subcultured and used for seeding 10 ml of minimum medium plus casamino acids (0.5%). After 20 hours of culture, the cells were centrifuged and the supernatant was dialysed against distilled water and concentrated by evaporation (centrifugation under vacuum).

Figure 12:
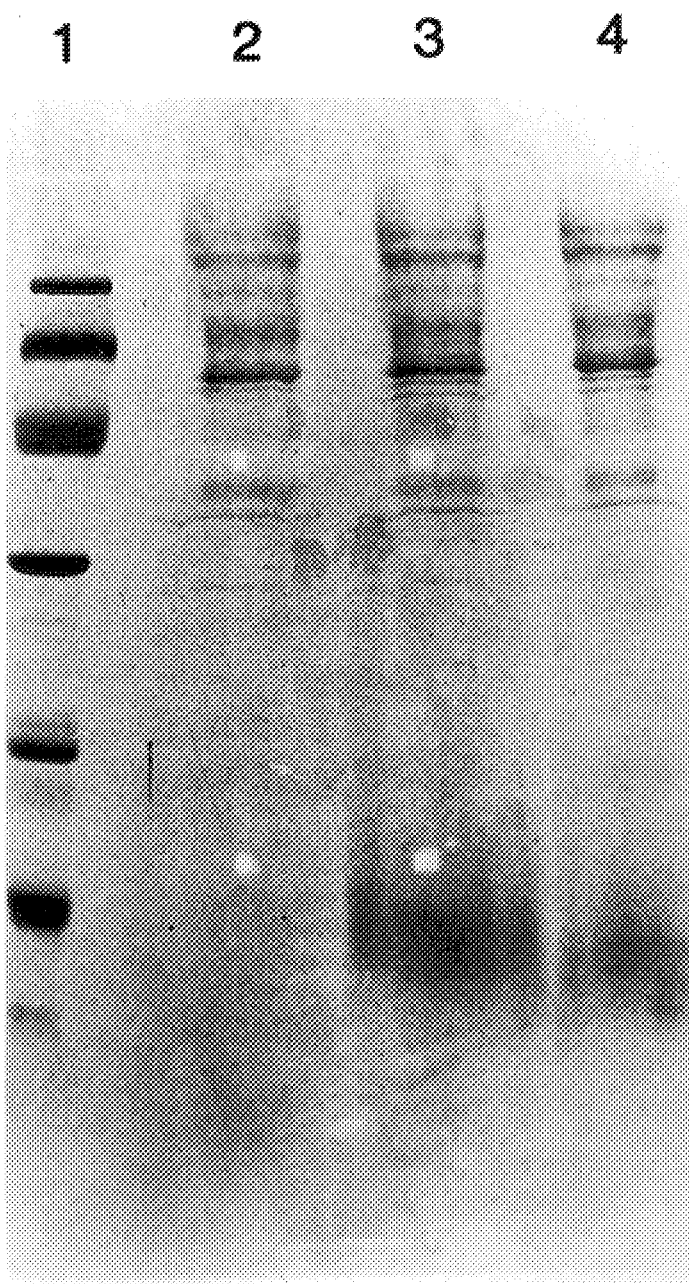
FIG. 12 shows an acrylamide gel electrophoresis of the proteins of MW>1,000 obtained in the medium after culturing yeasts transformed by pTG886 and pTG897.

In parallel, a TGY1sp4 culture transformed by pTG886 and a TGY1sp4 culture transformed by a plasmid not carrying a sequence for hirudin (TGY1sp4/pTG856) were treated in the same manner. The dry pellets were taken up in 50 μl of water and 20 μl were boiled in the presence of 2.8% SDS and 100 mM mercaptoethanol and then deposited on an acrylamide-SDS (15% acrylamide; 0.1% SDS) gel (21). After fixation and staining with Coomassie blue, polypeptides can be detected which accumulate in the culture supernatants of TGY1sp4/pTG886 and TGY1sp4/pTG897, and which are absent in the supernatant of the control culture (FIG. 12). In addition, these series of additional peptides are heavily labelled with [$^{35}$S]cysteine, as can be expected for hirudin peptides, this molecule being very rich in cysteine (FIG. 10).

Figure 13:
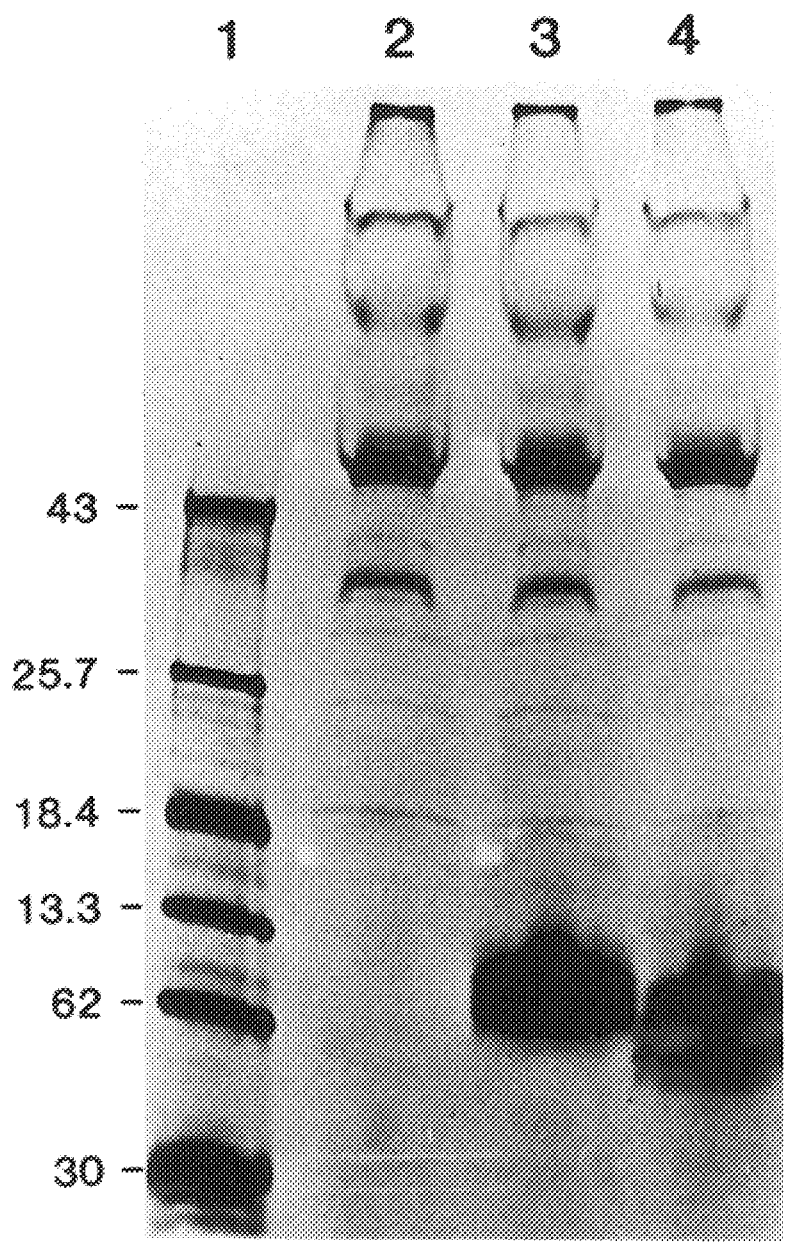
FIG. 13 shows an acrylamide gel electrophoresis of the proteins of MW>1,000 obtained in the medium after culturing yeasts transformed by pTG886 and pTG897.

The electrophoresis patterns shown in FIGS. 12 and 13 were produced as follows:

For FIG. 12, the extracts were prepared in the following manner: 10 ml of minimum medium (Yeast Nitrogen Base Difco without amino acid, (6.7 g/l) and glucose (10 g/l), supplemented with 0.5% casamino acids, were seeded with various strains and cultured for 20 hours (stationary phase). The cells were centrifuged and the supernatant dialysed against water (retention minimum: MW 1,000) and then dried by centrifugation under vacuum. The samples were then taken up with 50 μl of loading buffer, 20 of which were treated as described above, and deposited on acrylamide-SDS (15% acrylamide, 0.1% SDS) gel (21).

The strains used are:

well 2 : TGY1sp4 transformed by a plasmid not containing the hirudin sequence (control);

well 3 : TGY1sp4 transformed by pTG886:

well 4 : TGY1sp4 transformed by pTG897;

well 1 : the reference markers were deposited in well 1 (Pharmacia LMW kit; top to bottom: 94,000, 67,000, 43,000, 30,000, 20,100, 14,000).

The bands are visualized by staining with Coomassie blue R-250.

For FIG. 13, the extracts were prepared as folLows: 100 ml of minimum medium+40 µg/ml histidine were seeded with various strains for overnight cultures. When the cell density reaches approximately $5 \times 10^6$ (exponential growth phase), 40 µl of $^{35}$S cysteine (9.8 mCi/ml; 1,015 Ci/mmol) are added to each culture. After 10 minutes, the cells are centrifuged, taken up in 10 ml of complete medium (30° C.) and incubated at 30° C. with agitation. After 3 hours, the 10 ml of supernatant are dialysed against water and concentrated to a volume of 0.5 ml, as described for FIG. 12. ApproximateLy 35,000 cpm (40 µl) are deposited on acrylamide-SDS (15% acrylamide, 0.1% SDS) gel. The protein bands are visualized after fluorography.

The strains used are:

well 2 : TGY1sp4 transformed by a plasmid not containing the hirudin sequence;

well 3 : TGY1sp4 transformed by pTG886;

well 4 : TGY1sp4 transformed by pTG897;

well 1 : in well 1, markers were deposited having the MW indicated ($\times 10^3$).

However, when the supernatants containing these polypeptides were tested for their antithrombin activity, no activity could be detected.

In the case of the polypeptide excreted by TGY1sp4/pTG886, this is expected to undergo the normal stages of cleavage of the a pheromone precursor, which would give a hirudin molecule extended by 8 amino acids at its NH$_2$-terminal end. It is hence not surprising that the polypeptides secreted by the TGY1sp4/pTG886 cells is not active.

In contrast, in the case of a polypeptide secreted by TGY1sp4/pTG897, this polypeptide is expected to be identical to the natural protein, and hence active. Several hypotheses can account for the lack of activity:

1) Maturation of the protein is not complete, Glu-Ala residues possibly remaining at the NH$_2$ end, as has been described for EGF (14).

2) The protein is inactive because it does not have the correct conformation or alternatively because there are in the culture supernatant proteins or molecules of MW 1,000 which inhibit the activity.

3) The protein is incomplete because it has undergone an intracellular and/or extracellular proteolysis.

EXAMPLE 4

Activation by cleavage with cyanogen bromide

If the cause of the lack of activity is linked to the presence of additional amino acids at the NH$_2$-terminal end, it should be possible to retrieve the activity by subjecting the peptide secreted by TGY1sp4/pTG886 to cleavage with cyanogen bromide. This reagent is, in effect, specific for methionine residues and the fused protein encoded by pTGB86 only contains a single methionine. This reaction was performed in the following manner: yeasts containing either plasmid pTG886, or a control plasmid not comprising a hirudin insert, are cultured in 10 ml of medium for 24 hours. At this time, the culture reaches a density of 7 to $10 \times 10^7$ cells.ml$^{-1}$. The supernatant is separated from the cells, dialysed intensively against distilled water and then lyophilized. The dry powder is dissolved in 1 ml of 70% strength formic acid and an aliquot is used for the determination of total protein content (by the methods of staining with Coomassie blue, with the reagents sold by Biorad); the remainder of the preparation is treated with 1 ml of fresh cyanogen bromide solution (30 mg/mL) in 70% strength formic acid.

After removal of the oxygen by a stream of nitrogen, the tubes are incubated in the dark for 4 hours at room temperature. All the manipulations in the presence of cyanogen bromide are performed taking appropriate precautions and in a fume cupboard. The cleavage reaction by cyanogen bromide is stopped by adding 10 volumes of distilled water, and the solution is then lyophilized.

The cleaved peptides are redissolved in 10 ml of distilled water and re-lyophilized twice. Finally, the peptides are dissolved in a small volume of distilled water and an aliquot is used to measure the antithrombin activity. The remainder of the sample is lyophilized and subjected to the renaturation stages described below.

Since hirudin activity depends on the presence of disulphide bridges in molecule (1), it appears probable that the peptide cleaved with cyanogen bromide would have to be correctly renatured in order to show biological activity. The cleaved peptides were hence subjected to denaturat ion in 5M GuHCl, followed by renaturation, according to a method known to those versed in the art.

In summary, the lyophilized peptides are dissolved in 400 µl of 5M guanidinium chloride (GuHCl) in 250 mM Tris.HCl, pH 9.0; the solution is then made 2 mM in reduced glutathione and 0.2 mM in oxidized glutathione in a final volume of 2.0 ml (the final concentration is 1.0M GuHCl and 50 mM Tris).

After 16 hours' incubation at 23° C. in the dark, the samples are dialysed for 24 hours against 3 times 2 1 of 50 mM Tris.HCl, pH 7.5, 50 mM NaCl at 23° C., and the final dialysate is clarified by centrifugation.

The antithrombin activity of the supernatants is then measured. The result of this experiment, shown in Table I, shows clearly that there is a recovery of the antithrombin activity in the supernatants of the cells infected with plasmid pTG886, wherein there is no activity with the control plasmid.

TABLE I

ANTITHROMBIN ACTIVITY OF THE SUPERNATANTS OF YEAST CULTURES

| Plasmid | Treatment of the supernatant | Activity U/ml | Specific activity U/mg of initial proteins |
|---|---|---|---|
| pTG886 | a) after cleavage before renaturation | <0.3 | |
|  | b) after cleavage and renaturation | 2.46 | 102.5 |
| Control | a) after cleavage before renaturation | <0.3 | — |
|  | b) after cleavage and renaturation | <0.15 | <5.6 |

In conclusion, yeast cells carrying a recombinant plasmid can secrete a peptide having the biological activity of hirudin, after a cleavage and renaturation reaction. This shows that the presence of additional amino acids at the NH$_2$ terminal end would suffice to explain the lack of activity of the polypeptides present in the TGY1sp4/pTG886 cultures, and possibly also in the case of TGY1sp4/pTG897 cultures (Glu-Ala tails).

EXAMPLE 5

Introduction of a new cleavage site immediately before the first amino acid of the sequence coding for hirudin HV-2-plasmid pTG1805

Figure 2B:
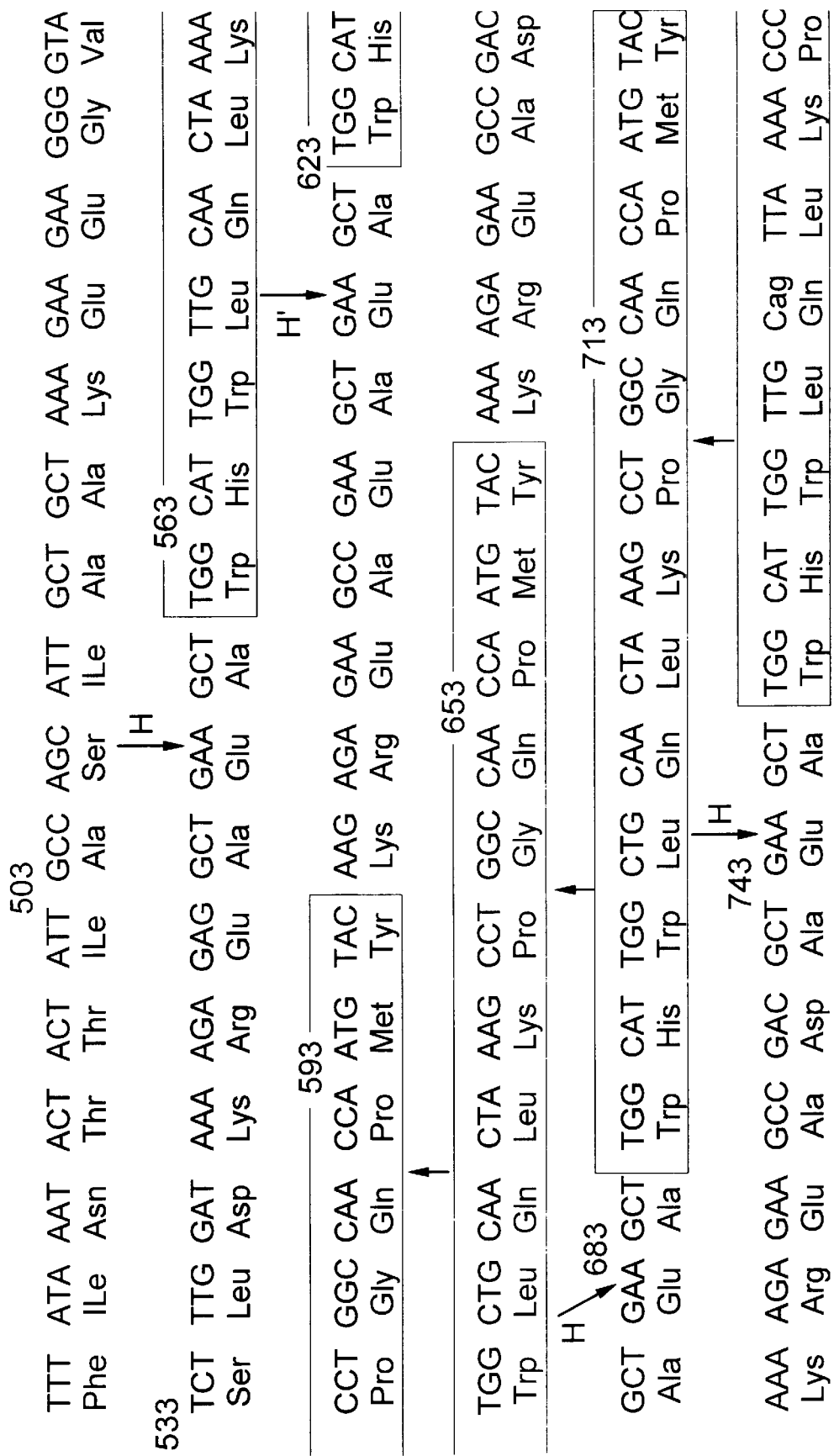
FIG. 2 shows the nucleotide sequence of the alpha sex pheromone precursor.
Figure 15:
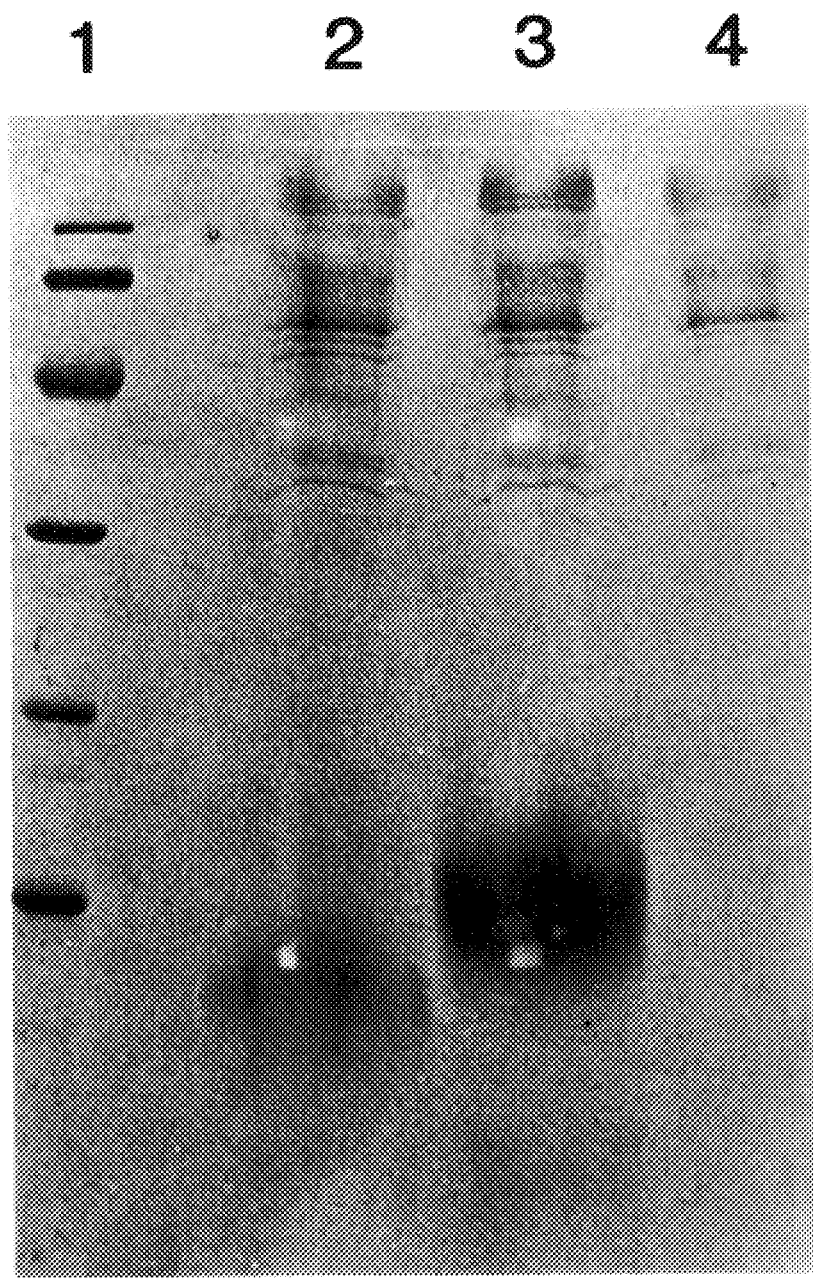
FIG. 15 shows an acrylamide gel electrophoresis of the proteins of MW>1,000 obtained in the medium after culturing yeasts transformed by pTG847 and pTG1805.

In the construction pTG897, there is a risk of the secreted peptide retaining its Glu-Ala tails at the $NH_2$ end, which would explain the lack of antithrombin activity in this material. If this hypothesis corresponds to the true situation, it should be possible to recover the activity directly in the supernatant by creating a cleavage site between the Glu-Ala residues and the first amino acid of hirudin HV-2 (isoleucine). This was carried out by adding a sequence coding for the Lys-Arg doublet, which is the recognition site for the endopeptidase involved in the maturation of the pheromone precursor (FIG. 2). The construction was obtained exactly as described for plasmid pTG897, except as regards the sequence of two synthetic oligonucleotides (FIG. 14). The resultant plasmid is referred to as pTG1805. The plasmid was used to transform the strain TGY1sp4 to ura$^+$. The material secreted into the supernatant was analysed by gel electrophoresis as described above, and compared with the material obtained with TGY1sp4/pTG897 (FIG. 15).

The strains used are:
well 1 : markers identical to those in FIG. 12;
well 2 : TGY1sp4 transformed by pTG897;
well 3 : TGY1sp4 transformed by pTG1805;
well 4 : control not producing hirudin.

The polypeptides specific to the strain TGY1sp4/pTG1805 migrate more slowly than those specific to the strain TGY1sp4/pTG897. This result suggests that the new cleavage site is not used efficiently by the corresponding endopeptidase. Nevertheless, the assay of hirudin in the supernatant on the basis of its biological activity reveals that a small portion of this material is active, in contrast to what is obtained with the cultures of TGY1sp4/pTG897, where the material is clearly inactive (Table II).

TABLE II

ANTITHROMBIN ACTIVITY OF THE SUPERNATANTS OF YEAST CULTURES (10 ml)

| Plasmid | Specific activity U/mg | Total activity U (10 ml) |
|---|---|---|
| pTG856 | not detectable | — |
| pTG897 | not detectable | — |
| pTG1805 | 21 | 2.0 |

EXAMPLE 6

New construction involving a new, more effective cleavage site, enabling mature hirudin to be liberated In the above construction (pTG897), only a small amount of hirudin activity was obtained in the supernatant, probably because the second cleavage site designed to liberate the mature hirudin is recognized inefficiently. A new construction was hence carried out, designed to make this additional cleavage site more susceptible to the endopeptidase, by adding to it, upstream, a sequence of the 3 amino acids Ser Leu Asp which is naturally present upstream of the first Lys-Arg doublet (FIGS. 2 and 16).

The technique used is the same as that described above, except as regards the oligonucleotides, the sequences of which are as follows:

The amino acid sequence in the cleavage region is shown in FIG. 16. The corresponding plasmid is referred to as pTG1818, and only differs form pTG1805 by the insertion of the nucleotides 5'-TTG GAT AAA corresponding to the codons Ser-Leu-Asp.

The activity assayed in the TGY1sp4/pTG1818 culture supernatants, following the standard conditions already described, is approximately 200 units per 10 ml of culture, equivalent to approximately 100-fold greater than that found in the preceding example. It should be noted that the assay can be carried out with 10 mL of unconcentrated culture medium.

EXAMPLE 7

Construction leading to the synthesis of a precursor devoid of Glu-Ala-Glu-Ala sequences In the above two examples, it was shown that the addition of a new Lys-Arg site immediately upstream from the beginning of the mature hirudin sequence enabled active material to be liberated into the supernatant. However, in these examples, while cleavage of the precursor takes place at the first Lys-Arg site (distal with respect to the beginning of the mature sequence), a heavier, inactive contaminant, corresponding to hirudin chains extended at the $NH_2$-terminal end, can be obtained in the culture medium. This is particularly clear in the case of the TGY1sp4/pTG1805 cultures, where the inactive contaminant predominates. This also remains likely in the case of the TGY1sp4/pTG1818 cultures, where the inactive contaminant does not predominate but could be present, as described by others in the case of EGF (1$_4$). To avoid this loss in yield represented by the synthesis of inactive material, it was decided to undertake a new construction leading to the synthesis of a precursor which only differs from that synthesized by TGY1sp4/pTG897 cells by the absence of the Glu Ala Glu Ala sequence between the Lys-Arg cleavage site and the first amino acid of the mature hirudin sequence.

The following strains were filed with the Collection Nationale de Cultures de Microorganismes (CNCM) (National Collection of Microorganism Cultures) of the INSTITUT PASTEUR, 28 rue du Docteur-Roux, PARIS 15 eme, on 30th April 1985:

TGY1sp4/pTG1818 : *Saccharomyces cerevisiae*, strain TGY1sp4 (MATα ura3-251-373-328-his 3-11-15) transformed to ura$^+$ by a plasmid pTG1818; filing no I 441.

TGY1sp4/pTG886 : *Saccharomyces cerevisiae*, strain TGY1sp4 (MATαura3-251-373-328-his 3-11-15) transformed to ura$^+$ by a plasmid pTG886; filing no I 442.

REFERENCES

1. BAGDY D., BARABAS E., GRAF L., PETERSEN T. E. and MAGNUSSON S. (1976) in Methods in Enzymology part B, vol. 45, pp. 669–678.
2. MARKWARDT F. (1970) Methods in Enzymology, eds.Perlman G. E. and Lorand L., Academic Press., vol. 19, pp. 924–932.

3. MARKWARDT F., HAUPTMANN J., NOWAK G., KLESSEN Ch. and WALSMANN P. (1982) Thromb. Hemostasis (Stuttgart) 47, 226–229.
4. WALSMANN P. and MARKWARDT F. (1981) Die Pharmazie 10, 653–660.
5. KLOSS Th. and MITTMANN U. (1982) Longenbecks Arch. Chirurg. 358, 548.
6. ISHIKAWA A., HAFTER R., SEEMULLER U., GOKEL J. M. and GRAEFF M. (1980) Thrombosis Research 19, 351–358.
7. MARKWARDT F., NOWAK G., STURZEBECKER J., GREISBADI U., WALSMANN P. and VOGEL G. (1984) Thromb. Hemostasis (Stuttgart) 52, 160–163.
8. NOWAK C. and MARKWARDT F. (1980) Expt. Path. 18, 438–443.
9. SUTOR A.H., KNOP S. et ADLER D. (1981) in Kontrolle Antithrombotica, 23rd Symp. Blutgerinnung, Hamburg, pp. 117–123.
10. PETERSEN T. E., ROBERTS H. R., SOTTRUP-JENSEN L., MAGNUSSON S. and BADGY D. (1976) Protides Biol. Fluids, Proc. Colloq. voL. 23, pp. 145–149.
11. CHANG J-Y. (1983) Febs Lett. 164, 307–313.
12. BASKOVA I. P., CHERKESOVA D. U. and MOSOLOV V. V. (1983) Thromb. Res. 30, 459–467.
13. BUSSEY H., SAVILLE D., GREENE D. et al. (1983) Mol. Cell. Biol. 3, 1362–1370.
14. BRAKE A. J., MERRYWEATHER J. P., COIT D. G., HEBERLEIN U. A., MARIARZ F. R., MULLENBACH G. T., URDEA M. S., VALENZUELA P. and BARR P. J. (1984) Proc. Natl. Acad. Sci. USA 81, 4642–4646.
15. BITTER G. A., CHEN K. K., BANKS A. R. and LAI P. H. (1984) Proc. Natl. Acad. Sci. USA 81, 5330–5334.
16. KURJAN J. and HERSKOWITZ I. (1982) Cell 30, 933–943.
17. BEGGS J. (1981) Genetic Engineering 2, 175–203.
18. BACH M. L., LACROUTE F. and BOTSTEIN D. (1979) Proc. Natl. Acad. Sci. (USA) 76, 386–390.
19. HITZEMAN R. A., HAGIE E. F., HAYFFLICK J. S. et al. (1982) Nucleic Acids Res. 10, 7791–7808.
20. ITO H., FUKUDA Y., MURATA K. and KIMURA A. (1983) J. Bacteriol. 153, 163–168.
21. LAEMMLI V. K. C. (1970) Nature 227, 680–685.
22. KRAMER W., DRUTSA V., JANSEN H. W. et al. (1984) Nucleic Acids Res. 12, 9441–9556.

We claim:

1. An expression cassette consisting of the sequence $S_{tr}$-$L_{ex}$-$H_{gene}$, wherein $S_{tr}$ is a DNA sequence which contains an expression control sequence functional in 1028 Saccharomyces;

$L_{ex}$ is a signal sequence required for obtaining secretion of a hirudin gene product; and $H_{gene}$ is the gene for hirudin or a variant of hirudin which exhibits the biological activity of hirudin which may be a precursor form of hirudin.

2. The expression cassette according to claim 1, wherein the sequence $L_{ex}$ encodes the α sex pheromone of yeast.

3. A plasmid vector which directs secretion of hirudin by a yeast comprising the expression cassette according to claim 1 and at least one origin of replication functional in yeast.

4. The expression cassette according to claim 1, wherein the H gene is followed by a yeast terminator sequence.

5. The expression cassette according to claim 4, wherein the yeast terminator sequence is that of the PGK gene.

6. A yeast comprising the expression cassette according to claim 1.

7. A process for preparing hirudin comprising:

fermenting yeast of claim 6 in a culture medium under conditions such that said $H_{gene}$ is expressed and hirudin is thereby produced; and recovering the hirudin produced in the culture medium which may be a hirudin precursor that can be processed to the mature form in vitro.

8. The expression cassette according to claim 1 further comprising a DNA sequence upstream of the $H_{gene}$ designated $S_{cl}$, which sequence codes for a peptide comprising a peptide site which can be enzymatically cleaved.

9. The expression cassette according to claim 8, wherein $S_{cl}$ is a sequence containing an ATG codon at the 3' end thereof, immediately upstream of the $H_{gene}$.

10. The expression cassette according to claim 8, wherein $S_{cl}$ is a sequence containing two codons which code for Lys-Arg at the 3' end thereof immediately upstream of $H_{gene}$.

11. The expression cassette according to claim 8, wherein $S_{cl}$ is a sequence containing five codons which code for Ser-Leu-Asp-Lys-Arg at the 3' end thereof immediately upstream of the $H_{gene}$.

12. A plasmid vector which directs secretion of hirudin by a yeast comprising the expression cassette according to claim 8 and at least one origin of replication functional in yeast.

13. The plasmid according to claim 12, wherein the origin of replication is that of the $2\mu$ plasmid.

14. The plasmid according to claim 12 further comprising a selection marker.

15. The plasmid according to claim 14, wherein the selection marker is the URA3 gene.

16. A yeast comprising the plasmid according to claim 12.

17. A process for preparing hirudin comprising;

fermenting the yeast claim 16 in a culture medium under conditions such that said $H_{gene}$ is expressed and hirudin is thereby produced;

recovering the hirudin produced in the culture medium in mature form or in the form of hirudin precursor, that can be processed to the mature form in vitro;

subjecting the precursor to chemical or enzymatic treatment so that cleavage of the sequence corresponding to $S_{cl}$ is effected; and renaturing the hirudin obtained after cleavage of the precursor.

18. The yeast according to claim 16, wherein said yeast is of the genus Saccharomyces.

19. The yeast according to claim 18, wherein said yeast possesses the Matα sex type.

20. The expression cassette according to claim 8 wherein said site can be recognized and cleaved by a yeast proteolytic enzyme.

21. The expression cassette according to claim 20 wherein said enzyme is a yeast proteinase which recognizes and cleaves Lys-Arg sequences.

22. A yeast comprising the expression cassette according to claim 8.

23. The yeast according to claim 22, wherein said yeast is of the strain S. cervisiae.

24. The yeast according to claim 22, wherein said yeast is of the genus Saccharomyces.

25. The yeast according to claim 24, wherein said yeast possesses the Matα sex type.

26. A process for preparing hirudin comprising:

fermenting the yeast of claim 22 in a culture medium under conditions such that said $H_{gene}$ is expressed and hirudin is thereby produced; and recovering the hirudin produced in the culture medium which may be a hirudin precursor that can be processed to the mature form in vitro.

27. Hirudin obtained by the process according to claim 26.

28. The hirudin according to claim 27, wherein said hirudin is labelled.

29. The hirudin product produced by the process according to claim 26 wherein said cleavage occurs after a methionine residue preceding the first amino acid of the hirudin precursor.

30. The hirudin product according to claim 29 wherein said cleavage occurs after the Lys-Arg or Ser-Leu-Asp-Lys-Arg sequence of the hirudin precursor.

31. The process according to claim 26, wherein the hirudin is in the precursor form.

32. The process according to claim 31, further comprising subjecting the precursor to chemical or enzymatic treatment so that cleavage of the sequence Lys Arg is effected.

33. The process according to claim 32, further comprising renaturing the hirudin obtained after cleavage of the precursor.

34. An expression cassette consisting of the sequence $S_{tr}$-$L_{ex}$-$H_{gene}$, wherein $S_{tr}$ is a DNA sequence which contains an expression control sequence functional in Saccharomyces;

$L_{ex}$ is a signal sequence required for obtaining secretion of a hirudin gene product; and $H_{gene}$ is the gene for hitudin or a variant of hirudin which exhibits the biological activity of hirudin which may be a precursor form of hirudin, wherein said cassette contains a DNA sequence upstream of the $H_{gene}$, designated $S_{cl}$, that codes for a peptide comprising a site which can be enzymatically cleaved, wherein said sequence is selected from the group consisting of;

Lys Arg Glu Ala Glu Ala Tip Leu Gln Val Asp Gly Ser Met;

Lys Arg Glu Ala Glu Ala;

Lys Arg Glu Ala Glu Ala Lys Arg;

Lys Arg Glu Ala Glu Ala Ser Leu Asp Lys Arg; and

Lys Arg.

35. An expression cassette consisting of the sequence $S^{tr}$-$L_{ex}$-$H_{gene}$, wherein $S_{tr}$ is a DNA sequence which contains an expression control sequence functional in Saccharomyces;

$L_{ex}$ is a signal sequence required for obtaining secretion of a hirdin gene product; and $H_{gene}$ is the gene for hirudin or a variant of hirudin which exhibits the biological activity of hirudin which may be a precursor form of hirudin and which consists of the nucleotide sequence shown in FIG. 1.

36. An expression cassette comprising a DNA sequence that contains an expression control sequence functional in Saccharomyces and a signal sequence required for obtaining secretion of a hirudin gene product operably linked to at least one sequence which codes for a series of amino acids selected from the group consisting of:

Lys Arg Glu Ala Glu Ala Trp Leu Gln Val Asp Gly Ser Met hirudin;

Lys Arg Glu Ala Glu Ala hirudin;

Lys Arg Glu Ala Glu Ala Lys Arg hirudin;

Lys Arg Glu Ala Glu Ala Ser Leu Asp Lys Arg hirudin and

Lys Arg hirudin.

* * * * *

UNITED STATES PATENT AND TRADEMARK OFFICE
CERTIFICATE OF CORRECTION

PATENT NO. : 5,821,079

DATED: : October 13, 1998

INVENTOR(S) : Gérard LOISON et al.

It is certified that error appears in the above-identified patent and that said Letters Patent is hereby corrected as shown below:

In claim 1, line 4, please delete "1028".

In claim 17, line 2, between "yeast" and "claim", please insert --of--.

In claim 34, line 14, please delete "Tip" and insert --Trp--.

In claim 35, line 2, please delete "$S^{tr}\text{-}L_{ex}\text{-}H_{gene}$" and insert --$S_{tr}\text{-}L_{ex}\text{-}H_{gene}$--.

Signed and Sealed this

Fourth Day of May, 1999

Attest:

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO. : 5,821,079
DATED : October 13, 1998
INVENTOR(S) : Gerard Loison, et. al.

It is certified that error appears in the above-identified patent and that said Letters Patent is hereby corrected as shown below:

Title page, item [73], Assignee: should read as following:

Behringwerke AG, Marburg, Germany.

Signed and Sealed this

Twenty-first Day of September, 1999

Attest:

Q. TODD DICKINSON

*Attesting Officer*  *Acting Commissioner of Patents and Trademarks*